(12) United States Patent
Justis

(10) Patent No.: US 9,060,817 B2
(45) Date of Patent: Jun. 23, 2015

(54) SYSTEMS AND METHODS FOR MINIMALLY INVASIVE SURGICAL PROCEDURES FO SYSTEMS

(71) Applicant: Warsaw Orthopedic, Inc., Warsaw, IN (US)

(72) Inventor: Jeff R Justis, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 196 days.

(21) Appl. No.: 13/655,106

(22) Filed: Oct. 18, 2012

(65) Prior Publication Data

US 2013/0041415 A1     Feb. 14, 2013

Related U.S. Application Data

(62) Division of application No. 12/715,908, filed on Mar. 2, 2010, now Pat. No. 8,323,286.

(51) Int. Cl.
*A61B 17/70* (2006.01)

(52) U.S. Cl.
CPC ........... *A61B 17/7085* (2013.01); *A61B 17/708* (2013.01); *A61B 17/7083* (2013.01); *A61B 17/7086* (2013.01)

(58) Field of Classification Search
CPC ............. A61B 17/7085; A61B 17/708; A61B 17/7083; A61B 17/7086
USPC ........ 606/86 A, 86 R, 250–265, 232, 279, 99, 606/914, 916, 278, 300–305
See application file for complete search history.

(56) References Cited

U.S. PATENT DOCUMENTS

| | | |
|---|---|---|
| 5,792,044 A | 8/1998 | Foley et al. |
| 6,530,929 B1 | 3/2003 | Justis et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,250,052 B2 | 7/2007 | Landry et al. |
| 7,306,603 B2 | 12/2007 | Boehm, Jr. et al. |
| 7,455,685 B2 | 11/2008 | Justis |
| 7,465,306 B2 | 12/2008 | Pond, Jr. et al. |
| 7,476,240 B2 | 1/2009 | Raymond et al. |
| 7,491,218 B2 | 2/2009 | Landry et al. |
| 7,497,869 B2 | 3/2009 | Justis |
| 7,520,879 B2 | 4/2009 | Justis et al. |
| 7,527,638 B2 | 5/2009 | Anderson |

(Continued)

*Primary Examiner* — Pedro Philogene
(74) *Attorney, Agent, or Firm* — Sorell Lenna & Schmidt LLP

(57) ABSTRACT

One nonlimiting embodiment of the present application is directed to a system for positioning a connecting element adjacent one or more bones or bony portions, such as the spinal column, through a minimally invasive surgical approach. The system generally includes a number of bone anchors engageable to the one or more bones or bony portions and a number of anchor extenders removably engaged to the bone anchors. A connecting element inserter instrument is engageable with one of the anchor extenders and is movable along a longitudinal axis of the anchor extender. As the inserter instrument is moved along the longitudinal axis toward the bone anchors, a leading end of the connecting element is rotated away from the longitudinal axis and the connecting element is positioned at a location adjacent the number of bone anchors in a minimally invasive surgical procedure. However, in other embodiments, different forms and applications are envisioned.

20 Claims, 22 Drawing Sheets

(56) References Cited

U.S. PATENT DOCUMENTS

| | | |
|---|---|---|
| 7,563,264 B2 | 7/2009 | Landry et al. |
| 7,563,274 B2 | 7/2009 | Justis et al. |
| 7,575,581 B2 | 8/2009 | Lovell |
| 7,648,507 B2 | 1/2010 | Techiera et al. |
| 7,691,132 B2 | 4/2010 | Landry et al. |
| 7,758,584 B2 | 7/2010 | Bankoski et al. |
| 7,815,664 B2 * | 10/2010 | Sherman et al. ............... 606/257 |
| 7,824,410 B2 | 11/2010 | Simonson et al. |
| 7,905,907 B2 | 3/2011 | Spitler |
| 7,909,830 B2 | 3/2011 | Frigg et al. |
| 7,914,558 B2 | 3/2011 | Landry et al. |
| 7,927,334 B2 | 4/2011 | Miller et al. |
| 7,985,242 B2 | 7/2011 | Forton et al. |
| 8,034,084 B2 | 10/2011 | Landry et al. |
| 8,048,124 B2 | 11/2011 | Chin et al. |
| 8,066,739 B2 | 11/2011 | Jackson |
| 8,075,592 B2 | 12/2011 | Landry et al. |
| 8,100,916 B2 | 1/2012 | Kumar et al. |
| 8,142,437 B2 | 3/2012 | McLean et al. |
| 8,147,524 B2 | 4/2012 | Piza Vallespir |
| 8,152,810 B2 | 4/2012 | Jackson |
| RE44,296 E * | 6/2013 | Beale et al. ............... 606/86 A |
| RE44,813 E * | 3/2014 | Beale et al. ............... 606/86 A |
| 2005/0171540 A1* | 8/2005 | Lim et al. ............... 606/61 |
| 2005/0192589 A1 | 9/2005 | Raymond et al. |
| 2006/0111713 A1 | 5/2006 | Jackson |
| 2007/0049931 A1 | 3/2007 | Justis et al. |
| 2007/0078460 A1 | 4/2007 | Frigg et al. |
| 2007/0233079 A1 | 10/2007 | Fallin et al. |
| 2007/0270867 A1 | 11/2007 | Miller et al. |
| 2008/0077139 A1 | 3/2008 | Landry et al. |
| 2008/0082103 A1 | 4/2008 | Hutton et al. |
| 2008/0200918 A1 | 8/2008 | Splitler et al. |
| 2008/0269805 A1 | 10/2008 | Dekutoski et al. |
| 2008/0319477 A1 | 12/2008 | Justis et al. |
| 2009/0163963 A1 | 6/2009 | Berrevoets |
| 2009/0234392 A1 | 9/2009 | Dziedzic et al. |
| 2009/0264930 A1 | 10/2009 | McBride |
| 2010/0249856 A1 | 9/2010 | Lott et al. |
| 2011/0022088 A1 | 1/2011 | Forton et al. |
| 2011/0046683 A1 | 2/2011 | Biedermann et al. |
| 2011/0184464 A1 | 7/2011 | Fiorella |
| 2011/0218581 A1 | 9/2011 | Justis |
| 2011/0313460 A1 | 12/2011 | McLean et al. |
| 2011/0319938 A1 | 12/2011 | Piza Vallespir et al. |
| 2012/0123477 A1 | 5/2012 | Landry et al. |

* cited by examiner

SYSTEMS AND METHODS FOR MINIMALLY INVASIVE SURGICAL PROCEDURES FO SYSTEMS

CROSS REFERENCE TO RELATED APPLICATIONS

The present application claims priority to and is a divisional of U.S. patent application Ser. No. 12/715,908 filed on Mar. 2, 2010 the contents of which is hereby incorporated by reference in its entirety.

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. However, there remains a need for further improvements in instruments, systems and methods for stabilizing bony structures using minimally invasive techniques.

SUMMARY

One nonlimiting embodiment of the present application is directed to a system for positioning a connecting element adjacent one or more bones or bony portions, such as the spinal column, through a minimally invasive surgical approach. The system generally includes a number of bone anchors engageable to the one or more bones or bony portions and a number of anchor extenders removably engaged to the bone anchors. A connecting element inserter instrument is engageable with one of the anchor extenders and is movable along a longitudinal axis of the anchor extender. In response to movement of the inserter instrument along the longitudinal axis toward the bone anchors, a leading end of the connecting element is rotated away from the longitudinal axis and the connecting element is positioned at a location adjacent the number of bone anchors. However, in other embodiments, different forms and applications are envisioned.

For example, another embodiment of the subject application is directed to a system for minimally invasive surgery that includes at least one bone anchor including a distal bone engaging portion and a proximal receiving portion. The system also includes at least one anchor extender extending along a longitudinal axis between a proximal end portion and a distal end portion configured to releasably engage with the at least one bone anchor. The at least one anchor extender also includes a proximally facing bearing surface. An inserter instrument including a connecting element engaging member is engageable with the at least one anchor extender and is movable along the longitudinal axis of the at least one anchor extender from the proximal end portion toward the distal end portion. A portion of the inserter instrument contacts the bearing surface as the inserter instrument is distally moved along the longitudinal axis of the at least one anchor extender and an orientation of the connecting element engaging member relative to the longitudinal axis changes in response to the portion of the inserter instrument contacting the bearing surface.

In yet another embodiment, a system for minimally invasive surgery includes a first bone anchor and a second bone anchor. Each of the first and second bone anchors includes a distal bone engaging portion and a proximal receiving portion. The system also includes a first anchor extender extending along a longitudinal axis between a proximal end portion and a distal end portion. The distal end portion includes a first pair of engaging members positioned opposite of a second pair of engaging members, and the first and second pairs of engaging members are configured to releasably engage with the first bone anchor. A second anchor extender extends along a longitudinal axis between a proximal end portion and a distal end portion that is configured to releasably engage with the second bone anchor. An inserter instrument is engageable with the first anchor extender and movable along the longitudinal axis of the first anchor extender from the proximal end portion toward the distal end portion to position a connecting element toward the proximal receiving portions of the first and second bone anchors. The system further includes a reduction instrument including a housing member releasably engageable with the proximal end portion of the second anchor extender. The reduction instrument also includes an elongated shaft axially displaceable relative to the housing member and the second anchor extender. As the inserter instrument is distally moved along the longitudinal axis of the first anchor extender, a leading end of the connecting element is rotated away from the longitudinal axis of the first anchor extender.

In another embodiment, an anchor extender includes an elongated body extending between a proximal end portion and a distal end portion. A first pair of engaging members is pivotably coupled with the elongated body adjacent the distal end portion. The first pair of engaging members is movable between a first configuration for receiving and releasing a first portion of a bone anchor and a second configuration for engaging the first portion of the bone anchor. The anchor extender also includes a second pair of engaging members pivotably coupled with the elongated body adjacent the distal end portion and opposite of the first pair of engaging members. The second pair of engaging members is movable between a first configuration for receiving and releasing a second portion of the bone anchor and a second configuration for engaging the second portion of the bone anchor. The anchor extender also includes a locking mechanism that is axially displaceable relative to the elongated body. In addition, the locking mechanism is configured to lock the first and second pairs of engaging members in the second configuration.

Another embodiment of the present application is a unique system for minimally invasive surgery in a patient. Other embodiments include unique methods, systems, devices, kits, assemblies, equipment, and/or apparatus involving minimally invasive surgical systems and techniques.

Further embodiments, forms, features, aspects, benefits, objects and advantages of the present application shall become apparent from the detailed description and figures provided herewith.

DESCRIPTION OF THE ILLUSTRATED EMBODIMENTS

Figure 1:
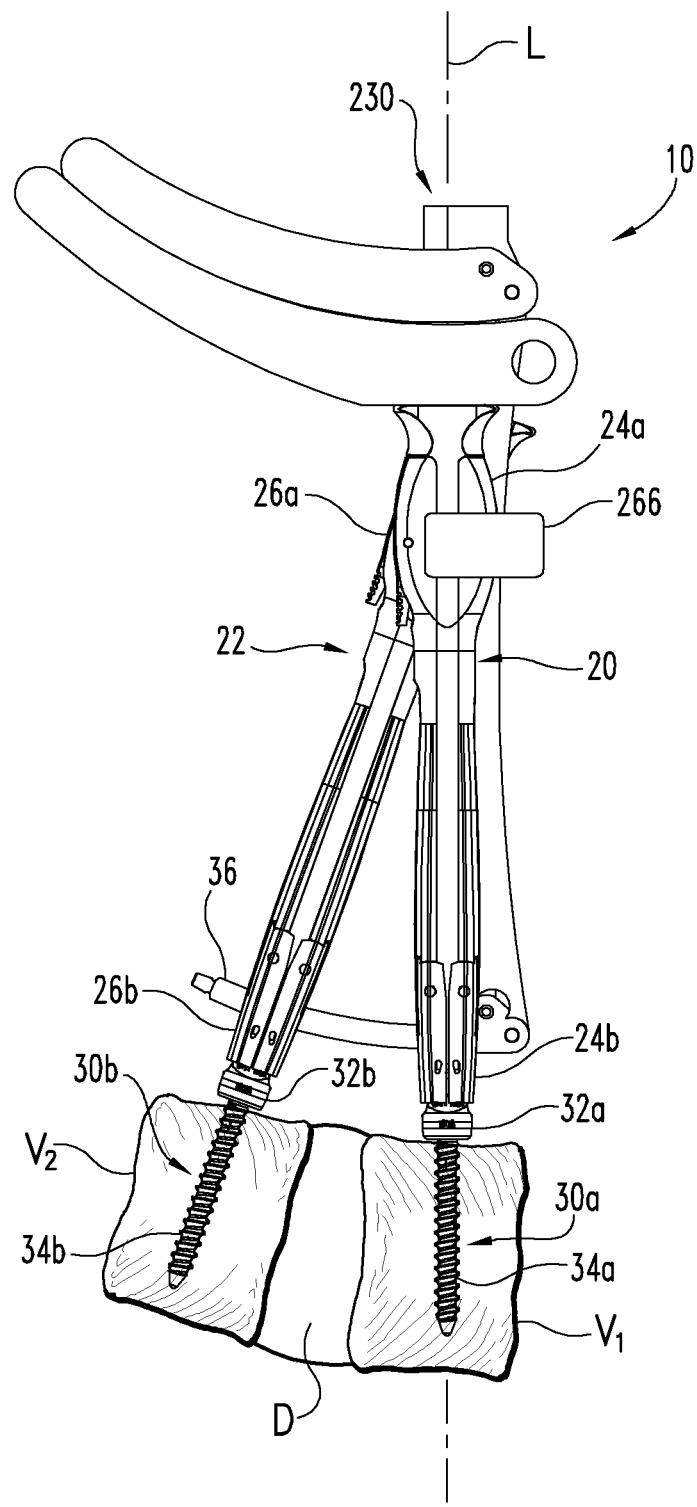
FIG. 1 is a side plan view of a system for positioning a connecting element in a patient in minimally invasive surgical procedures.
Figure 2:
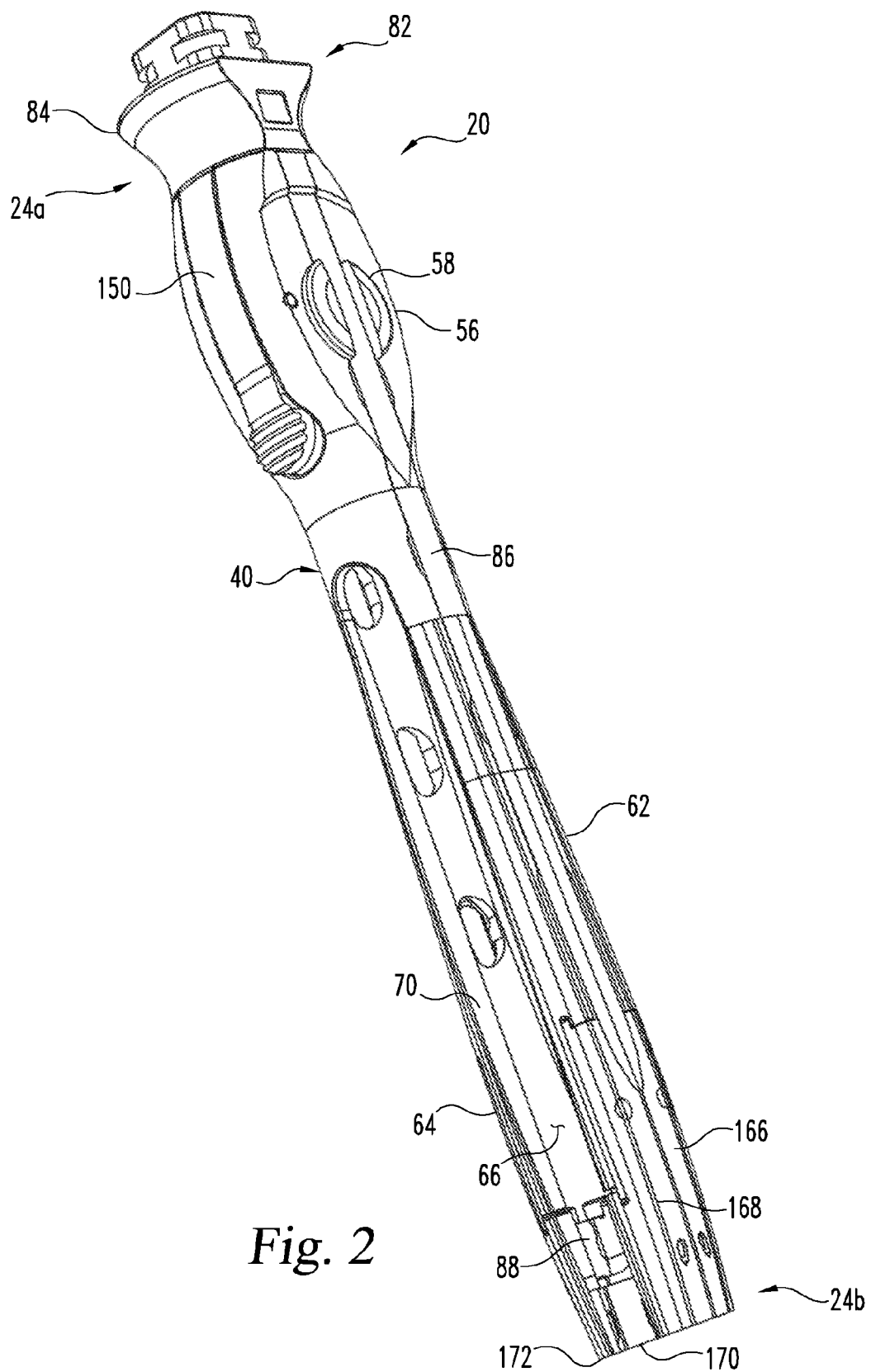
FIG. 2 is an enlarged, perspective view of an anchor extender of the system of FIG. 1.
Figure 3:
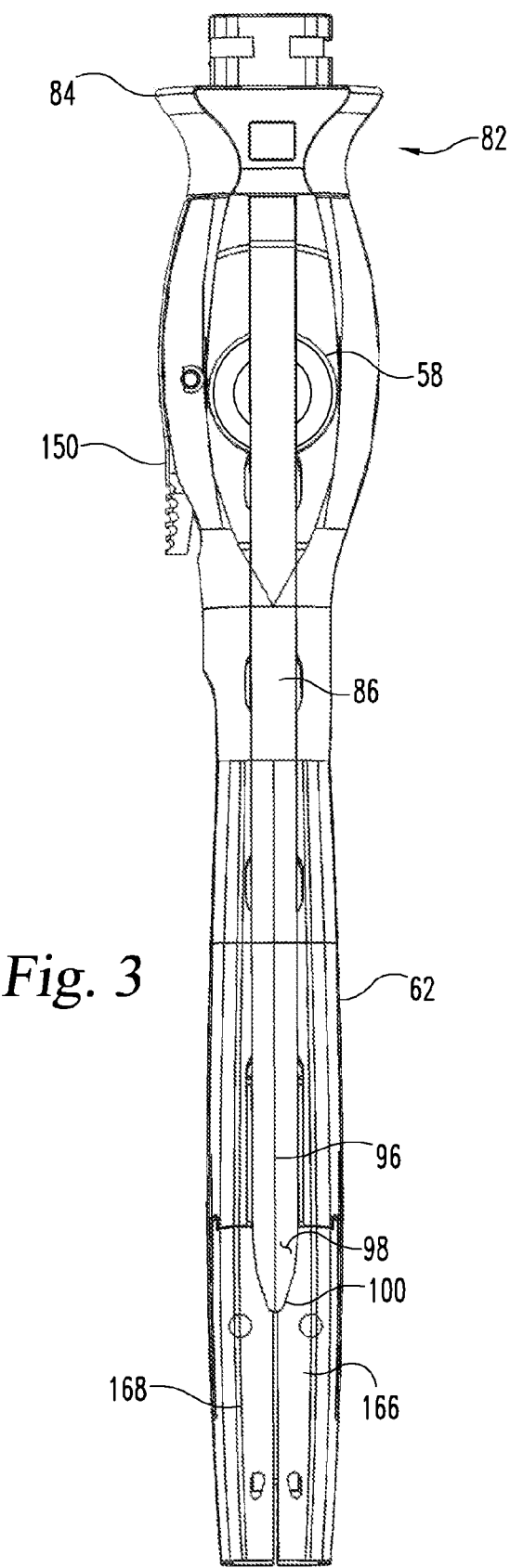
FIGS. 3-5 are alternative side plan views of the anchor extender of FIG. 2.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

The subject application is generally directed to systems for positioning a connecting element adjacent one or more bones or bony portions, such as the spinal column, through a minimally invasive surgical approach. The systems generally include a number of bone anchors engageable to the one or more bones or bony portions and a number of anchor extenders removably engaged to the bone anchors. A connecting element inserter instrument is engageable with one of the anchor extenders and is movable along a longitudinal axis of the anchor extender. In response to movement of the inserter instrument along the longitudinal axis toward the bone anchors, a leading end of the connecting element is rotated away from the longitudinal axis and the connecting element is positioned at a location adjacent the number of bone anchors. In one aspect of this arrangement, the inserter instrument engages with the anchor extender such that the connecting element is introduced to the location adjacent the number of bone anchors through the same incision through tissue and muscle in which the anchor extender is positioned. In addition, applications in non-minimally invasive surgeries are also contemplated.

Referring now to FIG. 1, there is shown a minimally invasive surgical system 10 that is positioned relative to a portion of the spinal column including adjacent vertebrae $V_1$, $V_2$ and a disc D positioned therebetween. It should be appreciated that use of system 10 in connection with more than two adjacent vertebrae or even at other anatomical locations besides the spinal column are also contemplated. System 10 includes two anchor extenders 20, 22 releasably mountable to respective ones of anchors 30a, 30b, a connecting element 36, a clamping member 266 engaged with anchor extenders 20, 22, and an inserter instrument 230. In other non-illustrated forms, system 10 may include one or more anchors and/or anchor extenders in addition to anchors 30a, 30b and anchor extenders 20, 22. Anchors 30a, 30b include proximal receiving portions 32a, 32b configured to receive connecting element 36 and a distal bone engaging portion 34a, 34b. In the illustrated embodiment, bone engaging portions 34a, 34b are bone screws with a threaded shank to engage the bony structure of the underlying vertebrae $V_1$, $V_2$. Proximal receiving portions 32a, 32b are receivers having a pair of opposing arms defining a longitudinal passage. The arms further define a proximally/distally extending opening that opens at a proximal end of the arms to receive a set screw (not shown) to secure connecting element 36 in the passage. Bone engaging portions 34a, 34b can be pivotally received in proximal receiving portions 32a, 32b through the distal openings thereof, and structured to interact therewith to provide anchors 30a, 30b with multi-axial capabilities that permit either a selected number of positions or infinitely numbered of positions of bone engaging portions 34a, 34b relative to proximal receiving portions 32a, 32b.

Other forms for anchors 30a, 30b are contemplated, including uni-axial and uni-planar forms. The bone engaging portion can also be in the form of a spike, staple, hook, fusion device, cannulated screw, fenestrated screw, interbody device, intrabody device, clamp, plate, suture anchor, bolt, pin or other bone engaging member. The receiving portion can be in the form of a saddle, yoke, eye-bolt or through-hole, side opening member, bottom opening member, top-opening member, eyelet, or any other structure engageable to connecting element 36.

In the illustrated embodiment, connecting element 36 is a rigid rod curved along an arc between its ends. However, it is contemplated that connecting element 36 can have a curvature that varies or is compounded along its length, or could be linear. In addition, in other forms it is contemplated that connecting element 36 can include any configuration known for a rod, implant, or fastener, so long as connecting element 36 is insertable using inserter instrument 230 in order to stabilize adjacent vertebrae $V_1$, $V_2$. Further, it is contemplated that connecting element 36 can be non-rigid, elastic and/or super-elastic and in the form of a cable, band, wire, or artificial ligament that is used in tethering, guiding, or other surgical procedures.

In the illustrated form of system 10, anchor extender 22 is configured the same as anchor extender 20. However, in other forms, it is contemplated that anchor extender 22 could be configured differently than anchor extender 20 so long as it facilitates engagement with clamping member 266 and introduction of connecting element 36 adjacent to anchors 30a, 30b. Non-limiting examples of alternative configurations for anchor extender 22 may be found in U.S. Pat. Nos. 6,530,929, 7,497,869 and 7,520,879 and in U.S. Patent Publication Nos. 2005/0171540 and 2008/0319477, just to provide a few possibilities. Furthermore, it is also contemplated that anchor extender 20 could be provided with a configuration different from that illustrated and described herein so long as it facilitates engagement with the inserter instruments described herein and introduction of connecting element 36 adjacent to anchors 30a, 30b.

Anchor extender 20 extends along a longitudinal axis L between a proximal end portion 24a and a distal end portion 24b configured to releasably engage with anchor 30a. Similarly, anchor extender 22 also extends between a proximal end portion 26a and a distal end portion 26b configured to releasably engage with anchor 30b. Further details regarding anchor extender 20 are described below in connection with FIGS. 2-13. As indicated above, anchor extender 22 is configured the same as anchor extender 20 in the illustrated form of system 10. Accordingly, it should be appreciated that the details provided below with respect to anchor extender 20 are also applicable to the illustrated form of anchor extender 22.

Figure 5:
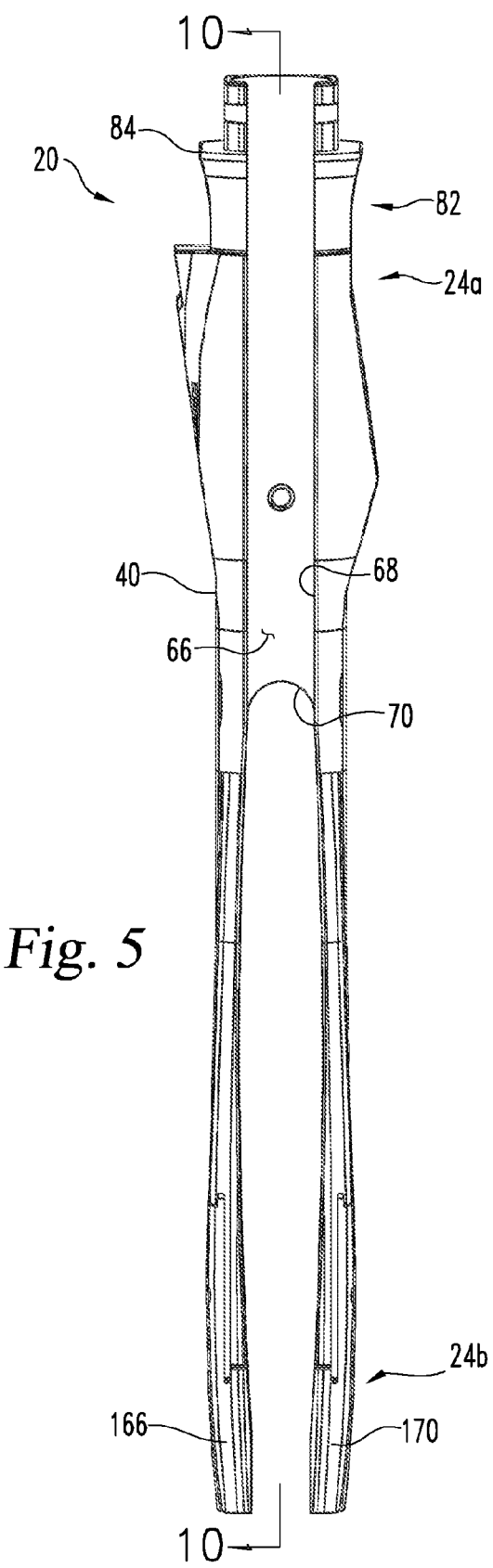
Figure 7:
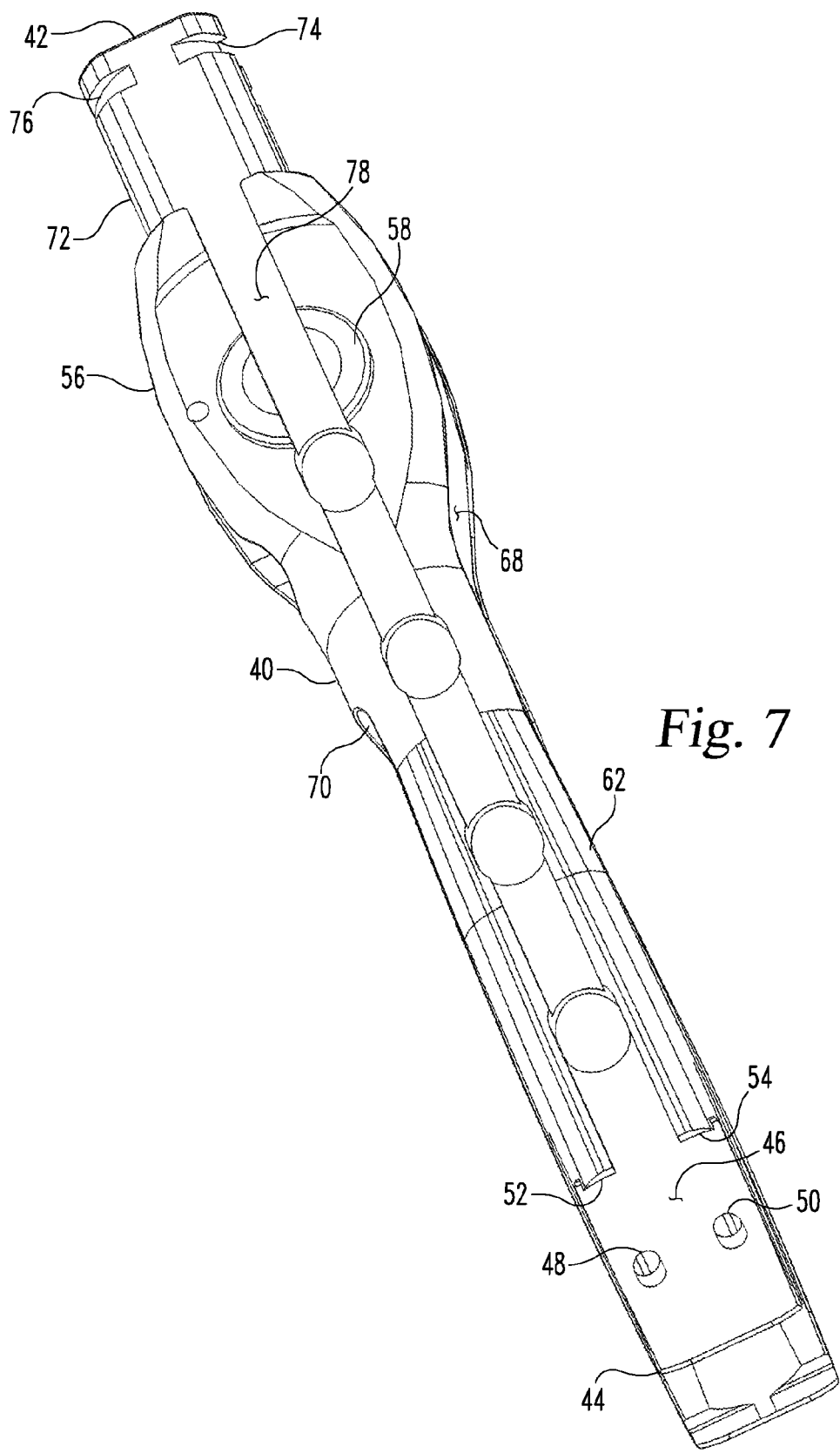
FIG. 7 is a perspective view of an elongated body of the anchor extender of FIG. 2.
Figure 8:
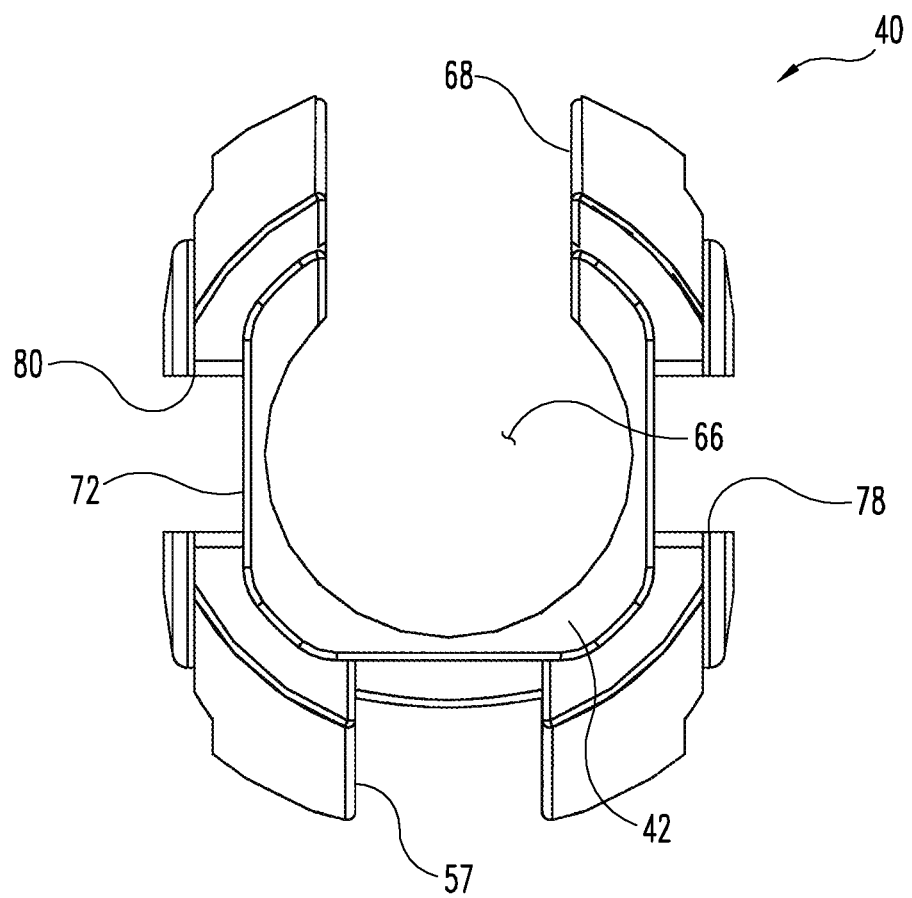
FIG. 8 is a plan view of an end of the elongated body illustrated in FIG. 7.

Anchor extender 20 generally includes an elongated body 40, a first pair of engaging members 166, 168, a second pair of engaging members 170, 172 positioned opposite of the first pair of engaging members 166, 168, a locking mechanism 82, and a retaining element 150. As illustrated in FIG. 7, where the first and second pairs of engaging members 166, 168 and 170, 172, locking mechanism 82 and retaining element 150 have been removed to enhance clarity, elongated body 40 extends between a proximal end 42 and a distal end 44. Elongated body 40 also includes a mounting surface 46 positioned adjacent to distal end 44. A first projection 48 and a second projection 50 extend from mounting surface 46 and are configured to engage with corresponding apertures 178, 192 in the first pair of engaging members 166, 168. Portions 52, 54 of elongated body 40 extend distally above a portion of mounting surface 46 and are configured to lie over a portion of engaging members 166, 168 in order to retain engaging members 166, 168 on elongated body 40 as best seen in FIG. 5 for example. In other forms, it is contemplated that engaging members 166, 168 could be coupled with elongated body 40 by a threaded interconnection with first and second projections 48, 50, although other variations for coupling engaging members 166, 168 to elongated body 40 are contemplated.

Figure 6:
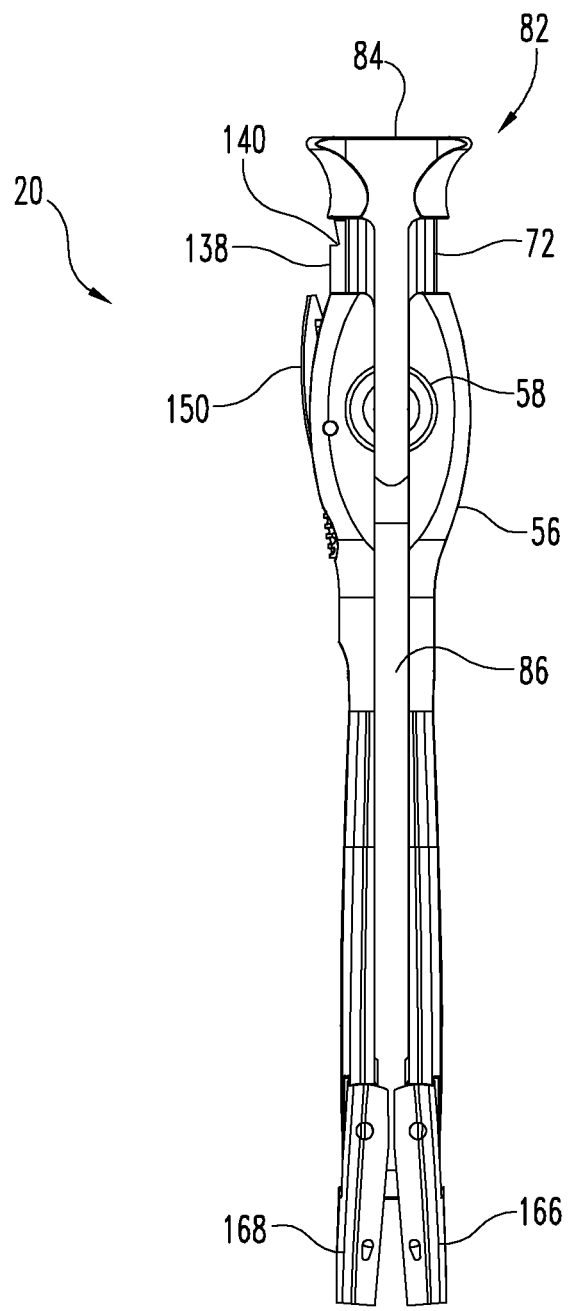
FIG. 6 is a side plan view of the anchor extender of FIG. 2 illustrating engaging members of the anchor extender in an open configuration.

Engaging members 166, 168 are pivotably rotatable relative to elongated body 40 about first and second projections 48, 50 between a first condition or position illustrated in FIG. 6 and a second condition or position illustrated in FIGS. 2-4 and 9 for example. In the first condition, engaging members 166, 168 are generally configured to permit a first one of the pair of opposing arms of receiving portion 32a of anchor 30a to be loaded between or ejected from engaging members 166, 168. In the second condition, the first one of the pair of opposing arms of receiving portion 32a of anchor 30a is securely positioned between engaging members 166, 168. Further details regarding engaging members 166, 168 will be provided below in connection with FIGS. 12 and 13. In addition, while not previously discussed, it should be appreciated that engaging members 170, 172 are engaged with and mounted on elongated body 40 in the same manner in which engaging members 166, 168 are engaged with and mounted on elongated body 40. Accordingly, engaging members 170, 172 are also pivotably rotatable relative to elongated body 40 between a first position or condition where a second one of the pair of opposing arms of receiving portion 32a of anchor 30a can be loaded between or ejected from engaging members 170, 172 and a second position or condition where the second one of the pair of opposing arms of receiving portion 32a of anchor 30a is securely positioned between engaging members 170, 172.

Elongated body 40 also includes an enlarged portion 56 positioned distally of proximal end 42. A groove 57 is formed along one side of enlarged portion 56 and is configured to receive and house retaining element 150 and a portion of a cap member 84 of locking mechanism 82. Enlarged portion 56 includes a pair of oppositely positioned cylindrical projections 58, 60 that are configured to engage with corresponding recesses in anchor extender 22 and clamping member 266. In alternative configurations, it is also contemplated that one or both of projections 58, 60 can be replaced by a cylindrical recess configured to engage with a corresponding projection in anchor extender 22 and/or clamping member 266. In addition, it should be appreciated that projections 58, 60 may also be non-cylindrically shaped. For example, it is contemplated that projections 58, 60 could be provided with a square, rectangular, or oval shape, just to name a few possibilities. Clamping member 266 is generally configured to engage with proximal end portions 24a, 26a of anchor extenders 20, 22 in order to clamp proximal end portions 24a, 26a of anchor extenders 20, 22 together during insertion of connecting element 36. In one form, clamping member 266 may be provided with a configuration that corresponds to a conventional C-clamp. However, in another form, it is contemplated that clamping member 266 may be configured similar to the clamping portion of the inserter disclosed in U.S. Patent Publication No. 2007/0049931, the contents of which are incorporated herein by reference in their entirety. Still, it should be appreciated that alternative configurations for clamping member 266 are also contemplated.

Elongated body 40 also includes a pair of leg members 62, 64 that extend distally from enlarged portion 56 and on which engaging members 166, 168 and 170, 172 are respectively mounted. Elongated body 40 generally includes a hollow interior 66 that extends between proximal end 42 and distal end 44. Oppositely positioned elongated slots 68, 70 are positioned between legs members 62, 64 and communicate with hollow interior 66. As best seen in FIG. 5, elongated slot 68 extends along the length of anchor extender 20 and opens proximally at proximal end portion 24a and distally at distal end portion 24b. Similarly, as illustrated in the end view of FIG. 8, elongated body 40 includes a U-shaped configuration in a plane traverse to the longitudinal axis L of anchor extender 20. In contrast to elongated slot 68, elongated slot 70 opens distally at distal end portion 24b, extends proximally toward proximal end portion 24a, and terminates at a position located distally of proximal end portion 24a. Elongated slots 68, 70 and hollow interior 66 generally cooperate to provide a passage for connecting element 36 to extend through anchor extender 20 as illustrated in FIG. 1.

Opposite of leg members 62, 64, a post member 72 extends proximally from enlarged portion 56 of elongated body 40. Post member 72 includes a pair of opposing grooves 74, 76 and is configured to receive a portion of locking mechanism 82. In addition, elongated body 40 also includes a pair of oppositely positioned elongated grooves 78, 80 that are configured to receive portions of locking mechanism 82, and that extend along leg members 62, 64 from enlarged portion 56 to locations adjacent engaging members 166, 168 and 170, 172. More particularly, locking mechanism 82 includes a cap member 84 and a pair of elongated locking members 86, 88 that are positioned in respective ones of elongated grooves 78, 80 and configured to interact and engage with engaging members 166, 168 and 170, 172, respectively. Further details regarding the interaction and engagement of elongated locking members 86, 88 with engaging members 166, 168 and 170, 172 are provided below in connection with FIGS. 12 and 13.

Figure 4:
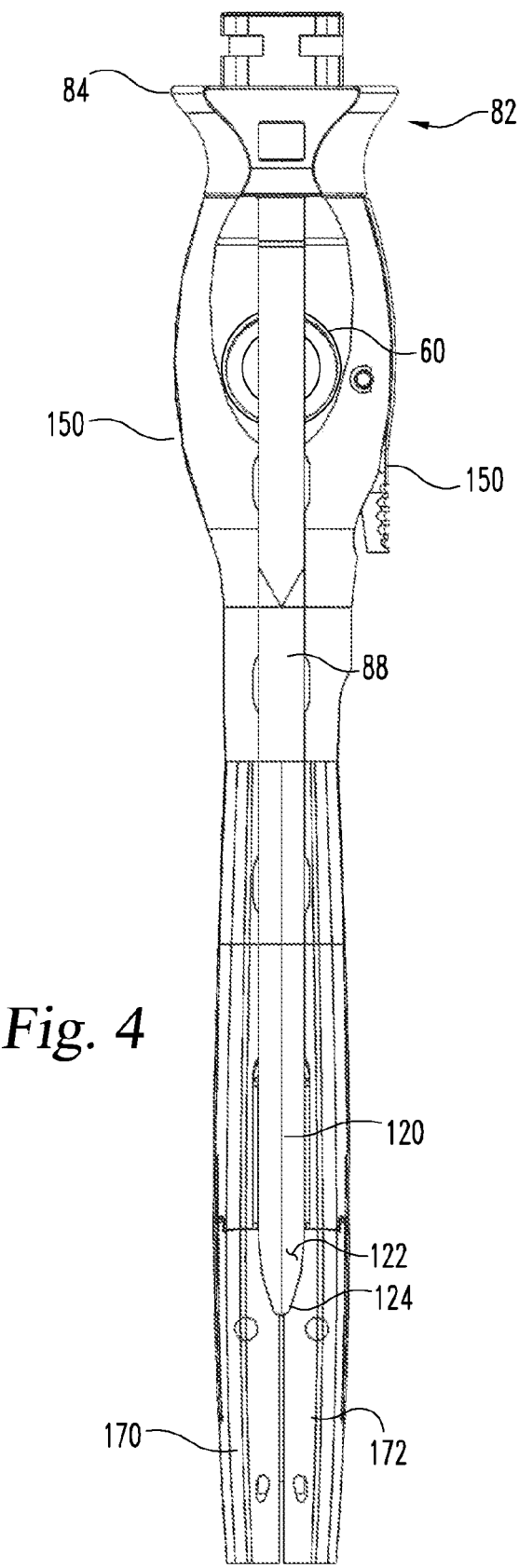
Figure 9:
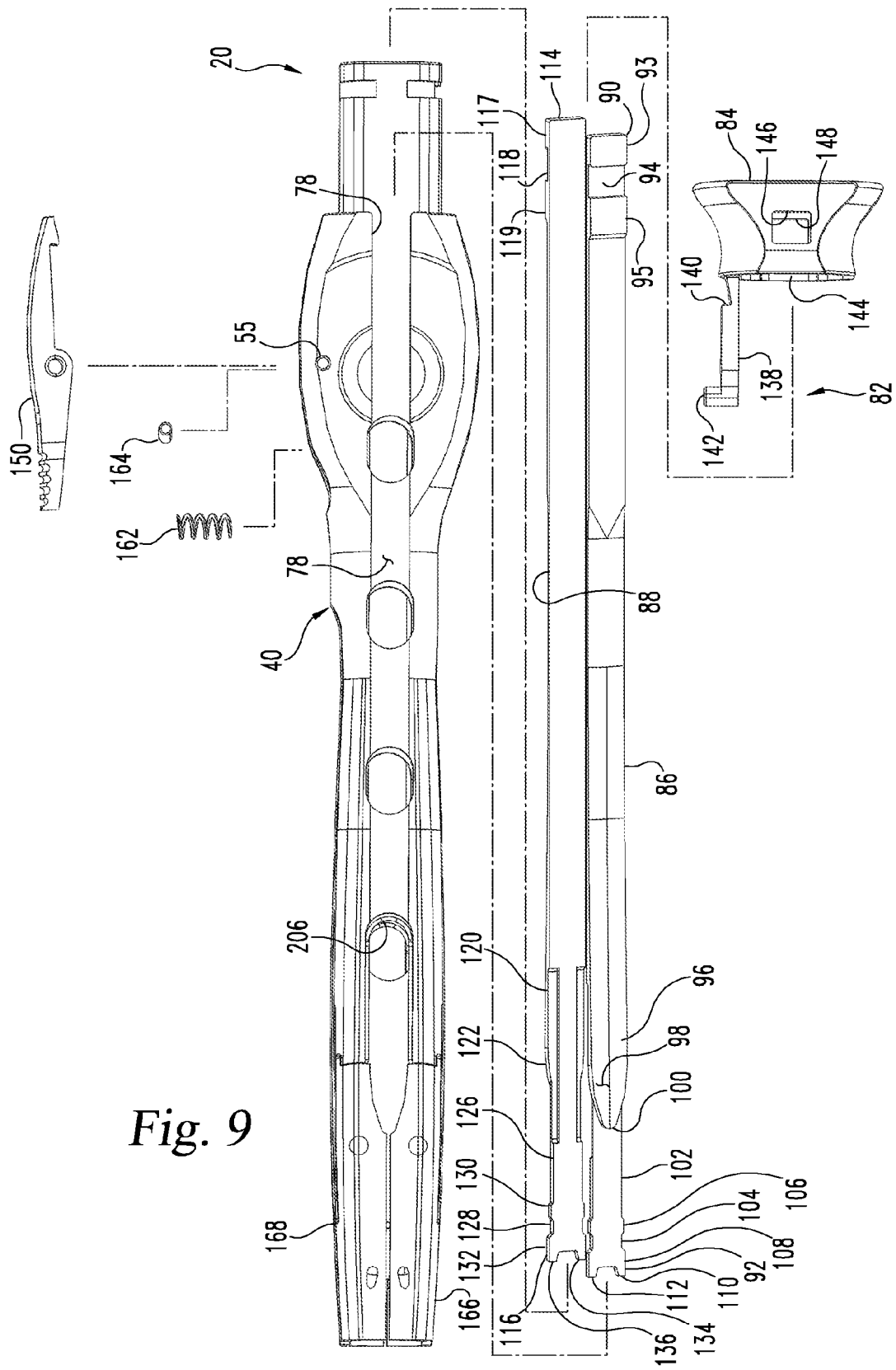
FIG. 9 is an exploded, partial assembly view of the anchor extender of FIG. 2.
Figure 10:
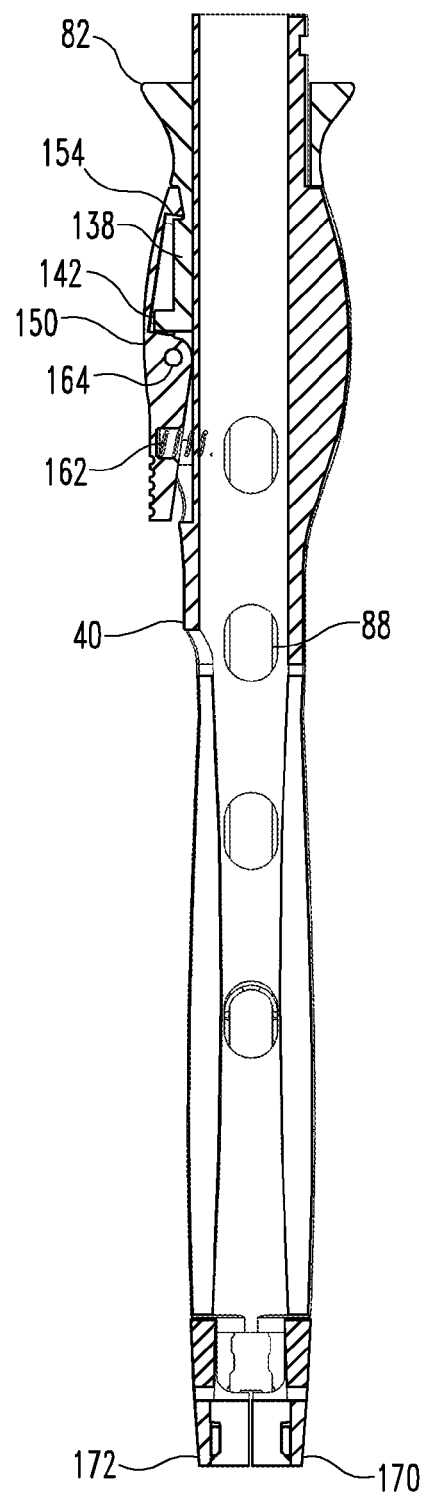
FIG. 10 is a section view along view line 10-10 of FIG. 5.

Elongated locking member 86 extends between a proximal end 90 and a distal end 92 and includes a notch 94 positioned adjacent to proximal end 90 and between increased thickness portions 93, 95. Elongated locking member 86 also includes a raised surface portion 96 positioned between proximal end 90 and distal end 92. As shown in FIG. 9 for example where a partial assembly view of anchor extender 20 is illustrated, raised surface portion 96 includes a tapered portion 98 that terminates at a point 100. A reduced thickness portion 102 extends distally from raised surface portion 96 and includes a notched portion 104 positioned between enlarged portions 106 and 108. Elongated locking member 86 also includes a pair of tabs 110, 112 extending distally from enlarged portion 108. Elongated locking member 88 extends between a proximal end 114 and a distal end 116 and includes a notch 118 positioned adjacent to proximal end 114 and between increased thickness portions 117, 119. Elongated locking member 88 also includes a raised surface portion 120 positioned between proximal end 114 and distal end 116. As shown in FIG. 4 for example, raised surface portion 120 includes a tapered portion 122 that terminates at a point 124. A reduced thickness portion 126 extends distally from raised surface portion 120 and includes a notched portion 128 positioned between enlarged portions 130 and 132. Elongated locking member 88 also includes a pair of tabs 134, 136 extending distally from enlarged portion 132.

Cap member 84 of locking mechanism 82 includes a distally extending stem 138 that includes a lateral facing notch 140 and a laterally facing projection 142. Cap member 84 also includes a passage 144 extending therethrough. Passage 144 communicates with a pair of opposing windows 146, 148 extending through side surfaces of cap member 84. In addition, passage 144 is also sized and configured to facilitate positioning of cap member 84 over post member 72 of elongated body 40.

Figure 11:
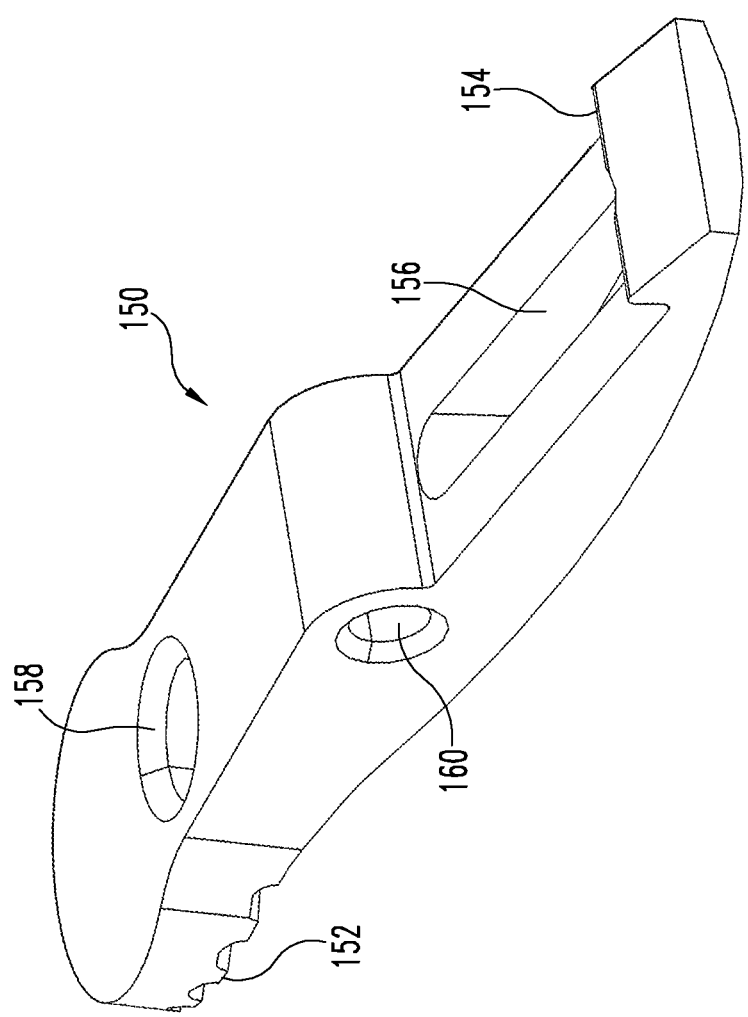
FIG. 11 is an enlarged, perspective view of a retaining member of the anchor extender of FIG. 2.

As indicated above, anchor extender 20 also includes a retaining element 150 which is shown in an enlarged, perspective view in FIG. 11. Retaining element 150 includes a user engagement portion 152 positioned opposite of a laterally extending lip 154. An elongated slot 156 is positioned adjacent to lip 154 and is configured to receive laterally facing projection 142 of cap member 84. Retaining element 150 also includes a recess 158 and a passage 160 positioned between user engagement portion 152 and lip 154.

With particular reference to FIG. 9, the remaining assembly of anchor extender 20 may be performed by positioning proximal ends 90, 114 of elongate locking members 86, 88 in cap member 84 such that increased thickness portions 93, 117 are positioned in windows 146, 148, respectively. Locking mechanism 82 may then be engaged with elongated body 40 by positioning elongated locking members 86, 88 in elongated grooves 78, 80 and distally advancing them toward engaging members 166, 168 and 170, 172 until post member 72 is positioned in passage 144 of cap member 84 and cap member 84 is adjacent to enlarged portion 56. When cap member 84 is positioned over post member 72, stem 138 is positioned in groove 57 of elongated body 40 and retaining element 150 can then be positioned over stem 138 in groove 57. A biasing element 162 is received in recess 158 and positioned between retaining element 150 and elongated body 40, and a retaining pin 164 is positioned through a passage 55 in enlarged portion 56 and passage 160 in order to couple retaining element 150 with elongated body 40. In this configuration, as best seen in the section view of FIG. 10, lip 154 of retaining element 150 is biased toward elongated body 40 such that it engages notch 140 on stem 138 when cap member 84 is positioned against enlarged portion 56 in order to lock the relative positioning of locking mechanism 82 and prevent proximal movement of the same. When cap member 84 is positioned against enlarged portion 56, elongated locking members 86, 88 engage with engaging members 166, 168 and 170, 172, respectively, and prevent their rotation relative to elongated body 40 such that release of anchor 30a from anchor extender 20 is prevented. As indicated above, further details regarding the relationship between locking members 86, 88 and engaging members 166, 168 and 170, 172 will be provided below in connection with FIGS. 12 and 13. In view of the foregoing, it should be appreciated that the engagement between lip 154 of retaining element 150 and notch 140 of cap member 84 prevents proximal movement of locking mechanism 82, as well as the release of anchor 30a from anchor extender 20.

When release of anchor 30a from anchor extender 20 is desired, user engagement portion 152 of retaining element 150 can be depressed to release lip 154 from notch 140 and allow proximal movement of locking mechanism 82. Similarly, as locking mechanism 82 is moved proximally to the position illustrated in FIG. 6 for example, engaging members 166, 168 and 170, 172 are able to pivot relative to elongated body 40 such that anchor extender 20 can be released from anchor 30a. Moreover, when retaining element 150 is coupled with elongated body 40, projection 142 extending laterally from stem 138 of cap member 84 is positioned in elongated slot 156. In this arrangement, when projection 142 comes into contact with the end of elongated slot 156 adjacent to lip 154, additional proximal movement of locking mechanism 82 is prevented. Similarly, it should be appreciated that the relationship between projection 142 and elongated slot 156 prevents removal of locking mechanism 82 from elongated body 40.

Figure 12:
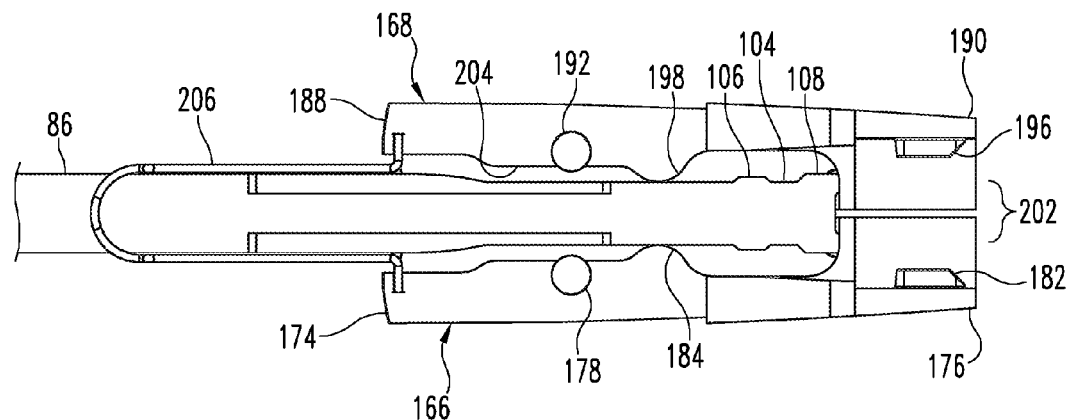
FIG. 12 is an enlarged, plan view of a distal portion of the anchor extender of FIG. 2.
Figure 13:
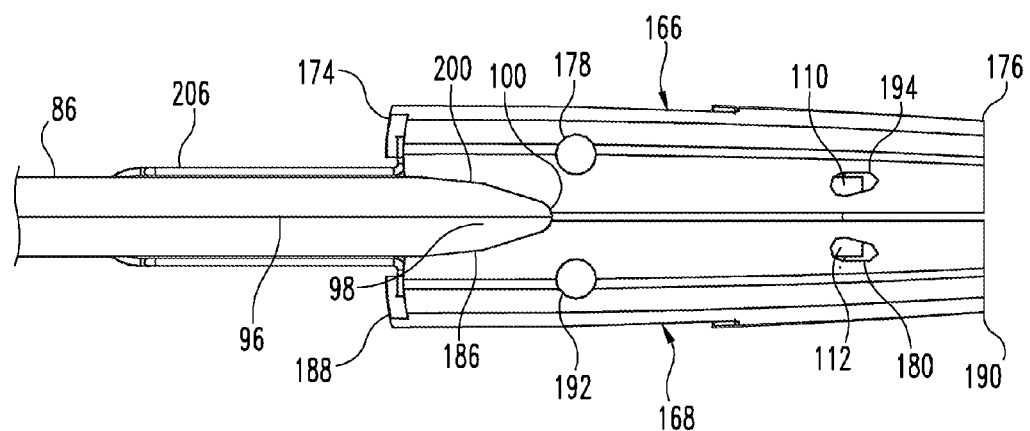
FIG. 13 is an alternative plan view of the distal portion illustrated in FIG. 12.

Referring now to FIGS. 12 and 13, further details of engaging members 166, 168 are shown in opposite side plan views. It should be appreciated that various features of anchor extender 20 have been omitted from FIGS. 12 and 13 in order to enhance clarity. In addition, it should also be appreciated that the description of features associated with engaging members 166, 168 is also applicable to engaging members 170, 172. Engaging member 166 extends between a proximal end 174 and a distal end 176 and includes an aperture 178 configured to be positioned over second projection 50 positioned on mounting surface 46 such that engaging member 166 is pivotable about second projection 50. Engaging member 168 extends between a proximal end 188 and a distal end 190 and includes an aperture 192 configured to be positioned over first projection 48 positioned on mounting surface 46 such that engaging member 168 is pivotable about first projection 48. Engaging members 166 and 168 cooperate to define a receptacle 202 configured to receive a portion of one arm of the pair of opposing arms of proximal receiving portion 32a of anchor 30a. Moreover, engaging members 166 and 168 each include a projection 182, 196, respectively, that extends into receptacle 202 and is configured to engage with a corresponding recess (not shown) formed in the arm of the proximal receiving portion 32a of anchor 30a. A biasing element 206 is positioned between engaging members 166, 168 adjacent to proximal ends 174, 188 and forces proximal ends 174, 188 away from one another such that distal ends 176, 190 are normally positioned adjacent one another in the configuration illustrated in FIGS. 12 and 13.

Engaging members 166, 168 also cooperate to define a channel 204 which receives elongated locking member 86. As shown in FIGS. 12 and 13, locking member 86 is positioned in engagement with locking members 166, 168. More particularly, as locking member 86 is moved distally along elongated body 40, tapered portion 98 of raised surface portion 96 is positioned in a recess between engaging members 166, 168 and engages with correspondingly shaped surfaces 186, 200 on engaging members 166, 168 until point 100 is positioned against engaging members 166, 168. As locking member 86 is moved in this manner, tapered portion 98 applies an additional spreading force to proximal ends 174, 188, which in turn also forces distal ends 176, 190 toward each other. Moreover, once point 100 is positioned against engaging members 166, 168, raised surface portion 96 prevents movement of proximal ends 174, 188 toward each other such that distal ends 176, 190 can not be moved away from each other. In addition, engaging members 166, 168 also each include a receptacle 180, 194, respectively, which receive tabs 110, 112 of locking member 86 when point 100 is positioned against engaging members 166, 168. Tabs 110, 112 cooperate with receptacles 180, 194 in a manner that also prevents separation of distal ends 176, 190 of engaging members 166, 168. Similarly, when anchor extender 20 is engaged with anchor 30a, the engagement of tabs 110, 112 with receptacles 180, 194 prevents release of anchor 30a from engaging members 166, 168.

Engaging members 166, 168 also each include a rounded surface 184, 198 which extends into channel 204. As elongated locking member 86 is moved proximally relative to engaging members 166, 168, rounded surfaces 184, 198 pass over enlarged portion 106 and become seated in notched portion 104. In this configuration, enlarged portions 106 and 108 are positioned on opposite sides of rounded surfaces 184, 198 such that the position of elongated locking member 86 relative to elongated body 40 and engaging members 166, 168 is provisionally locked or retained until a force sufficient to move notched portion 104 away from rounded surfaces 184, 198 is applied to locking mechanism 82.

Figure 14:
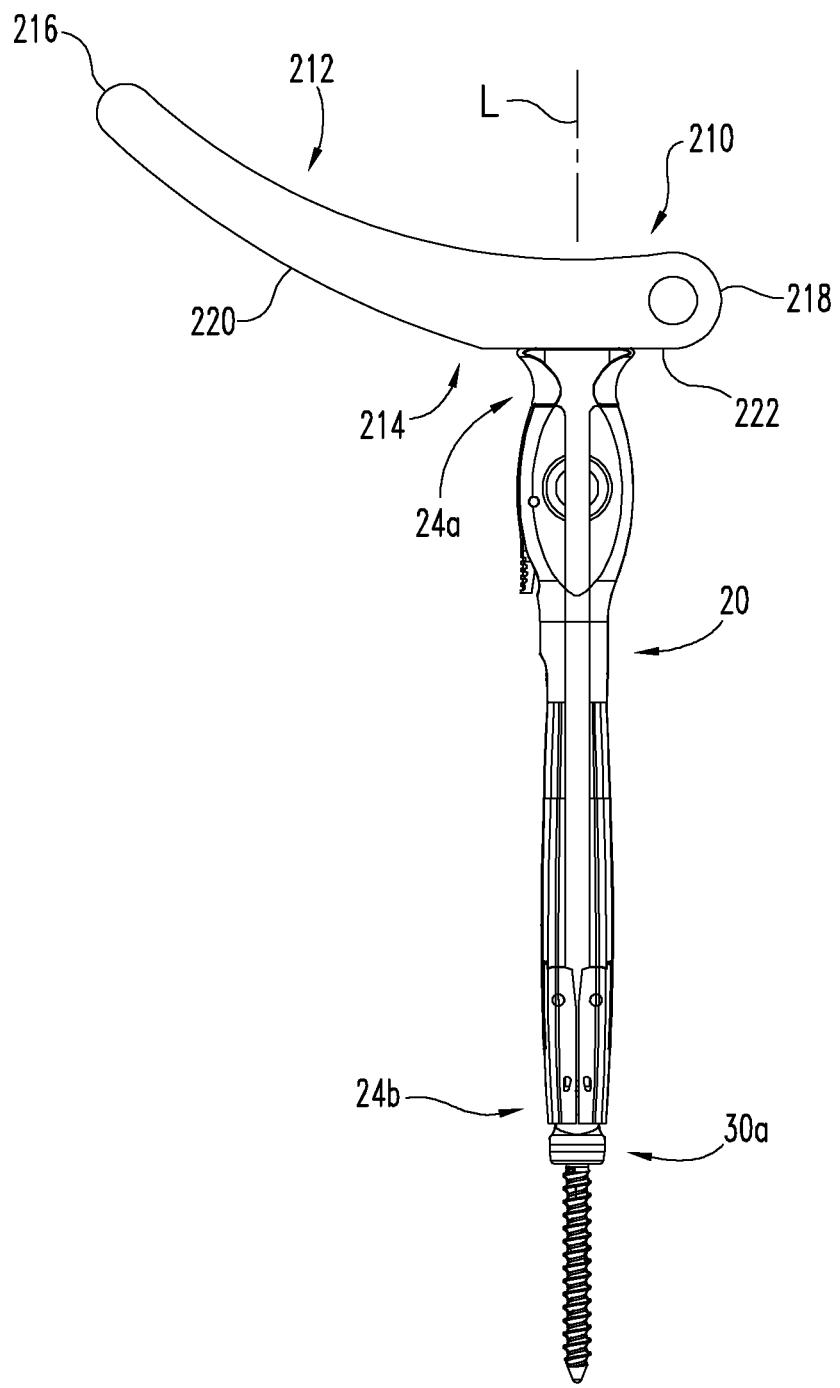
FIG. 14 is a side plan view of the anchor extender of FIG. 2 engaged with a bone anchor and including a platform member coupled therewith.

As illustrated in FIG. 14, distal end portion 20b of anchor extender 20 is engaged with anchor 30a and a platform member 210 is positioned on proximal end portion 24a of anchor extender 20. More particularly, platform member 210 includes a passage configured to be positioned over and receive post member 72 of elongated body 40. In one form, it is contemplated that platform member 210 can be releasably coupled with post member 72 through a friction or press fit. Alternatively, platform member 210 can be provided with a locking member, such as a set screw or snap ring, which engages with a portion of post member 72 in order to secure platform member 210 on post member 72, although other configurations for coupling platform member 210 with post member 72 are contemplated. Platform member 210 includes a proximal bearing surface 212 and an oppositely positioned distal surface 214. Surfaces 212, 214 extend between a first end 216 and a second end 218 of platform member 210. As illustrated in FIG. 14, platform member 210 extends laterally from anchor extender 20 such that first end 216 is laterally offset from the longitudinal axis L of anchor extender 20.

Distal surface 214 generally includes a convexly curved portion 220 and a linear portion 222 that is positioned adjacent to cap member 84 of locking mechanism 82. In addition, proximal bearing surface 212, which is configured to engage with a portion of inserter instrument 230, is concavely curved between first end 216 and second end 218. In the illustrated form, the curvature of proximal bearing surface 212 between first end 216 and second end 218 is varied. More particularly, the curvature of proximal bearing surface 212 adjacent first end 216 is greater than the curvature of proximal bearing surface 212 adjacent second end 218, although embodiments where the curvature between first end 216 and second end 218 is constant are also contemplated. In other non-illustrated forms, it is contemplated that proximal bearing surface 212 can be linear or provided with a non-continuous curvature; i.e., it can include one or more linear portions in combination with one or more curved portions. Still, in other forms, it is contemplated that system 10 can be provided with a plurality of platform members 210 that each includes an alternatively configured proximal bearing surface 212. In this arrangement, the orientation of engagement between inserter instrument 230 and proximal bearing surface 212 is adjustable, and a user can select an appropriately arranged platform member 210 to be used with a connecting element 36 having a specific curvature and/or to alter the insertion path of connecting element 36 as will be discussed in greater detail below with regard to FIGS. 16-20.

Figure 15:
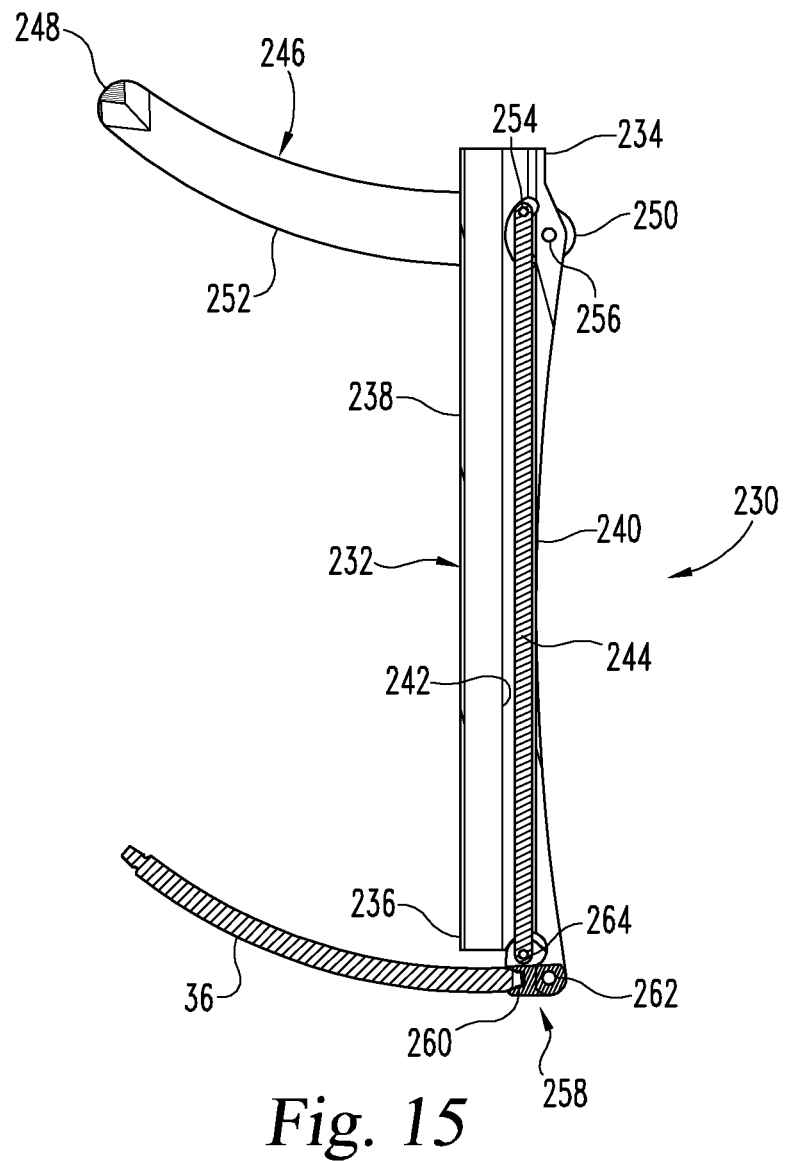
FIG. 15 is a section view of an inserter instrument of the system of FIG. 1.
Figures 16, 17, 18, 19, 20:
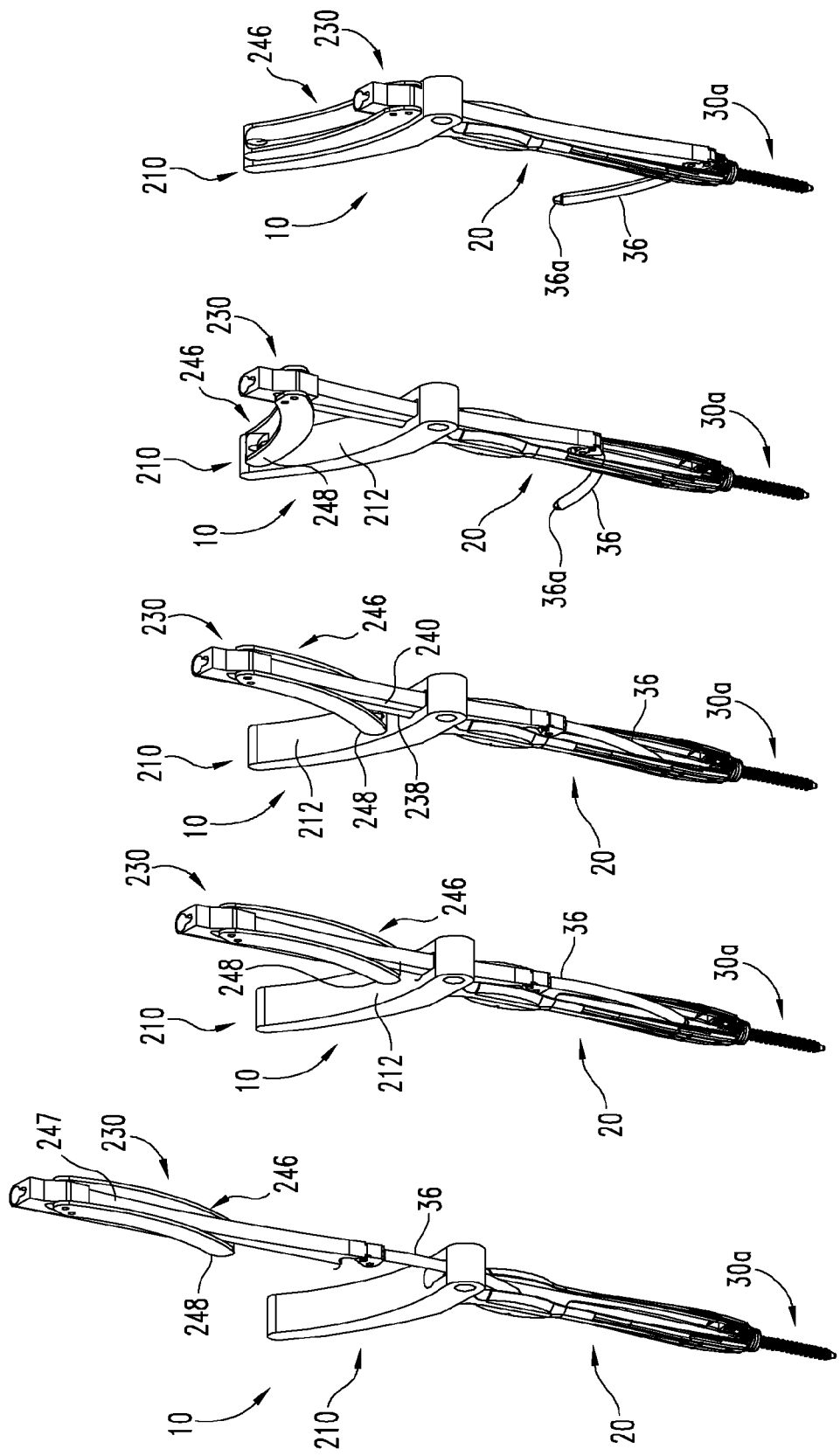
FIGS. 16-20 illustrate various steps of a minimally invasive surgical procedure for inserting a connecting element with the system illustrated in FIG. 1.

Inserter instrument 230 is shown in a section view in FIG. 15, and in a perspective view relative to anchor extender 20 in FIGS. 16-20. Inserter instrument 230 includes an elongated housing 232 that extends between a proximal end 234 and a distal end 236. As best seen in FIG. 18 for example, elongated housing 232 includes a first portion 238 that has a generally arcuate configuration and is positioned opposite of a second portion 240 that has a generally rectangular configuration. Similarly, when inserter instrument 230 is engaged with anchor extender 20, first portion 238 is received in hollow interior 66 of elongated body 40 while second portion 240 is positioned in and extends laterally through elongated slot 68 such that rotation of inserter instrument 230 relative to anchor extender 20 is prevented. Inserter instrument 230 also includes an elongated passage 242 within which a linking member 244 is positioned. Linking member 244 extends between a lever arm 246 and a connecting element engaging member 258. Lever arm 246 extends between a first end 248 and a second end 250 and includes a convexly curved surface 252. Second end 250 is pivotably coupled with a first end of linking member 244 by a pivot pin 254 and to elongated housing 232 by a pivot pin 256.

Connecting element engaging member 258 includes a receptacle 260 which releasably engages and receives an end of connecting element 36. In one form, it is contemplated that receptacle 260 engages the end of connecting element 36 through a friction or press fit, although it should be appreciated that variations in the engagement between connecting element 36 and receptacle 260 are contemplated. Connecting element engaging member 258 is coupled with linking member 244 by a pivot pin 264 and to elongated housing 232 by a pivot pin 262. In this arrangement, connecting element engaging member 258 is rotated relative to elongated housing 232 in response to rotation of lever arm 246 relative to elongated housing 232. More particularly, as first end 248 of lever arm 246 is moved away from elongated housing 232, linking member 244 is moved proximally in passage 242 such that connecting element engaging member 258 is rotated away from elongated housing 232 and extends transversely to elongated housing 232 as illustrated in FIG. 15. Similarly, when connecting element 36 is received in receptacle 260 and the orientation of connecting element engaging member 258 relative to elongated housing 232 is changed, the orientation of connecting element 36 relative to elongated housing 232 also changes. Moreover, while not illustrated in FIG. 15, it should be appreciated that when first end 248 of lever arm 246 is rotated toward elongated housing 232, linking member 244 is moved distally in passage 242 such that connecting element engaging member 258 is also rotated toward elongated housing 232 and may be positioned in an orientation where it extends in general alignment with elongated housing 232. Accordingly, when connecting element 36 is received in receptacle 260 and connecting element engaging member 258 is positioned in this orientation, connecting element 36 will also extend in general alignment with elongated housing 232.

FIGS. 16-20 generally illustrate various steps of inserting connecting element 36 with inserter instrument 230 of system 10 relative to anchor extender 20 which is engaged with anchor 30a. In FIG. 16 for example, connecting element 36 is coupled with connecting element engaging member 258 of inserter instrument 230 and extends through platform member 210 into a portion of hollow interior 66 of anchor extender 20. In this arrangement, connecting element 36 generally extends in-line with the longitudinal axis of anchor extender 20. Moreover, lever arm 246 includes an elongated receptacle 247 that receives a portion of elongated housing 232 such that first end 248 of lever arm 246 is positioned against elongated housing 232. As indicated above, connecting element 36 in the illustrated form is generally curved along an arc between its opposite ends. Similarly, as illustrated in FIG. 16, connecting element 36 can be arranged relative to inserter instrument 230 such that the concave side of connecting element 36 is oriented toward anchor extender 20.

With connecting element 36 initially positioned into hollow interior 66 as illustrated in FIG. 16, inserter instrument 230 can be moved distally such that first portion 238 and second portion 240 of elongated housing 232 are received in hollow interior 66 and elongated slot 68, respectively, of elongated body 40 of anchor extender 20. As inserter instrument 230 is moved distally relative to anchor extender 20 in this manner, first end 248 of lever arm 246 comes into contact with proximal bearing surface 212 of platform member 210 as illustrated in FIG. 17. FIG. 18 illustrates further distal movement of inserter instrument 230 relative to anchor extender 20, and corresponding distal movement of connecting element 36 in hollow interior 66. As inserter instrument 230 is moved in this manner, first end 248 of lever arm 246 bears against and engages with proximal bearing surface 212 of platform member 210, and is directed away from elongated housing 232. Similarly, lever arm 246 is rotated away from elongated body 232 and connecting element engaging member 258 and connecting element 36 are correspondingly rotated away from elongated housing 232. Upon further distal movement of inserter instrument 230 relative to anchor extender 20, first end 248 of lever arm 246 is moved further away from elongated housing 232 until it is positioned adjacent to first end 216 of platform member 210. Similarly, as first end 248 of lever arm 246 is moved across proximal bearing surface 212 toward this position, connecting element engaging member 258 and connecting element 36 are correspondingly rotated away from elongated housing 232 such that a leading end 36a of connecting element 36 extends through anchor extender 20 and toward another anchor, such as anchor 30b illustrated in FIG. 1.

Figure 28:
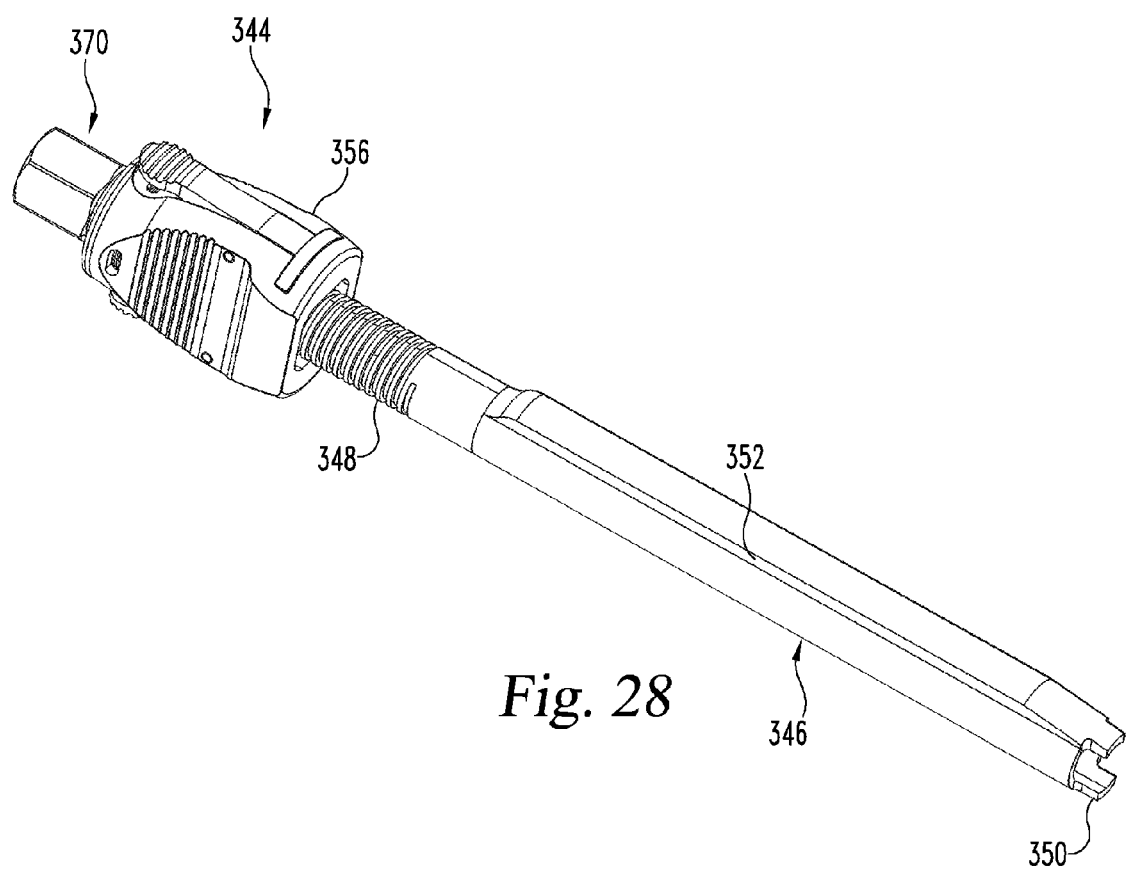
FIG. 28 is a perspective view of a reduction instrument usable in the system of FIG. 1.
Figure 29:
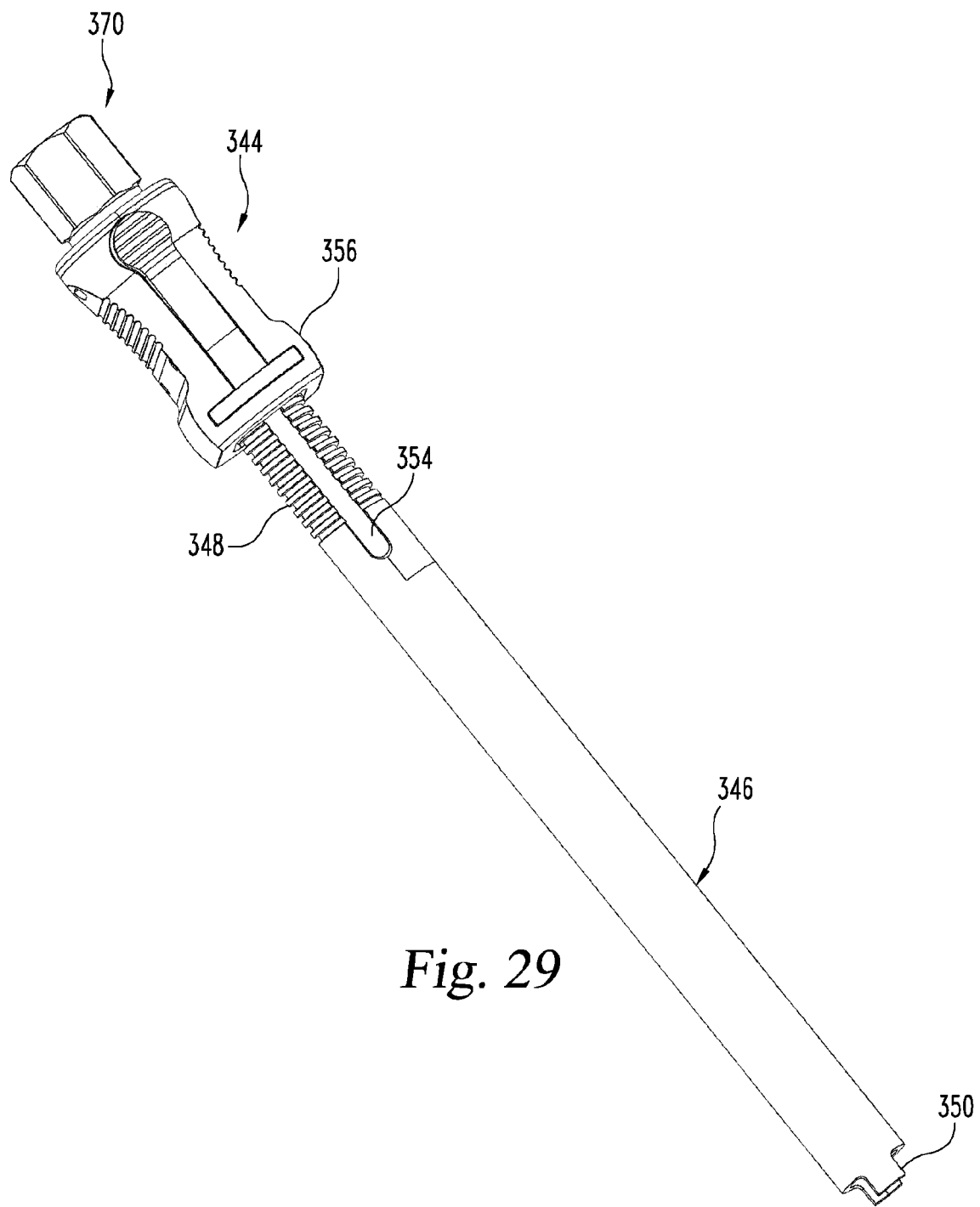
FIG. 29 is an alternative perspective view of the reduction instrument of FIG. 28.

As illustrated in FIGS. 1 and 20, upon additional distal movement of inserter instrument 230 relative to anchor extender 20, convex surface 252 of lever arm 246 comes to rest against proximal bearing surface 212 of platform member 210 until further distal movement of inserter instrument 230 relative to anchor extender 20 is eliminated. In addition, connecting element engaging member 258 is further rotated away from anchor extender 20 such that it and connecting element 36 generally extend transversely to anchor extender 20. In this arrangement, the orientation of connecting element 36 has been rotated about ninety degrees relative to its initial orientation illustrated in FIG. 16. In addition, as illustrated in FIG. 1, connecting element 36 is also generally aligned so that it can be reduced into proximal receiving portions 32a, 32b of anchors 30a, 30b. Once connecting element 36 is arranged in this manner, a reduction instrument, such as instrument 344 illustrated in FIGS. 28-30, can be engaged with and inserted through anchor extender 22 in order to reduce connecting element 36 into proximal receiving portions 32a, 32b of anchors 30a, 30b. After connecting element 36 has been engaged by reduction instrument 344, inserter instrument 230 can be moved proximally relative to anchor extender 20 to release connecting element 36 from receptacle 260 of connecting element engaging member 258. Once connecting element 36 is released, inserter instrument 230 can be removed from anchor extender 20 and reduction of connecting element 36 into proximal receiving portions 32a, 32b of anchors 30a, 30b can be completed.

Following reduction of connecting element 36 in proximal receiving portions 32a, 32b of anchors 30a, 30b, a locking member, such as a set screw for example, may be introduced through each of anchor extenders 20, 22 and engaged with proximal receiving portions 32a, 32b of anchors 30a, 30b to secure connecting element 36 relative to anchors 30a, 30b. In one form, it is contemplated that the locking members could be engaged with proximal receiving portions 32a, 32b at the same time. However, in another form, a first locking member can be inserted through anchor extender 20 and engaged with proximal receiving portion 32a while reduction instrument 344 is engaged with anchor extender 22 and engaged against connecting element 36. Reduction instrument 344 can then be removed from anchor extender 22 followed by the introduction of a second locking member through anchor extender 22 into engagement with proximal receiving portion 32b of anchor 30b in order to lock connecting element 36 in proximal receiving portion 32b.

As illustrated in FIGS. 1 and 16-20, inserter instrument 230 is generally moved relative to anchor extender 20 along its longitudinal axis L. However, in other non-illustrated forms it is contemplated that inserter instrument 230 and/or anchor extender 20 could be configured such that inserter instrument 230 is movable along an axis or pathway that extends transversely or obliquely to longitudinal axis L of anchor extender 20. Moreover, in view of the foregoing description of inserter instrument 230, it should be appreciated that inserter instrument 230 inserts connecting element 36 along a partially curved path of insertion. More particularly, leading end 36a of connecting element 36 is simultaneously moved proximally and laterally away from anchor extender 20 as connecting element engaging member 258 is rotated relative to elongated housing 232. Among other things, this arrangement may allow leading end 36a of connecting element 36, and eventually connecting element 36, to extend through and/or below tissue between anchors 30a, 30b in order to allow positioning of connecting element 36 while avoiding cutting and/or removing this tissue. However, in other forms, it is contemplated that connecting element 36 could also be inserted along a curvilinear or linear insertion path dependent on its configuration and/or the configuration of platform member 210 and inserter instrument 230. Moreover, it should be appreciated that the relationship between proximal bearing surface 212 and lever arm 246 will generally control the rate at which connecting element engaging member 258 is rotated relative to elongated housing 232 as inserter instrument 230 is moved distally relative to anchor extender 20. This relationship may also potentially control the amount connecting element engaging member 258 is rotated relative to elongated housing 232.

For example, when proximal bearing surface 212 is provided with a greater amount of curvature between first end 216 and second end 218, first end 248 of lever arm 246 will be advanced adjacent to first end 216 upon relatively less distal movement of inserter instrument 230 relative to anchor extender 20, which will in turn provide increased rotation of connecting element engaging member 258 relative to elongated housing 232 upon the relatively same amount of distal movement of inserter instrument 230. In addition, movement of lever arm 246 along proximal bearing surface 212 in this arrangement may also increase the total amount of rotation of connecting element engaging member 258 relative to elongated housing 232. As another example, if proximal bearing surface 212 is provided with a linear configuration or a smaller amount of curvature between first end 216 and second end 218, first end 248 of lever arm 246 will be advanced adjacent to first end 216 upon relatively more distal movement of inserter instrument 230 relative to anchor extender 20, which will in turn provide decreased rotation of connecting element engaging member 258 relative to elongated housing 232 upon the relatively same amount of distal movement of inserter instrument 230. In addition, movement of lever arm 246 along proximal bearing surface 212 in this arrangement may also decrease the total amount of rotation of connecting element engaging member 258 relative to elongated housing 232. It should also be appreciated that the configuration of surface 252 of lever arm 246 may be changed in order to alter the rotation properties of connecting element engaging member 258. Amongst other things, it may be desirable to change the relationship between proximal bearing surface 212 and lever arm 246 dependent on the anatomical location where connecting element 36 is being inserted and/or the curvature of connecting element 36. Thus, when system 10 is provided with a plurality of platform members 210 that each includes an alternatively configured bearing surface 210 as discussed above, a user may select a platform member 210 that will provide a relationship between platform member 210 and lever arm 246 that is most suited for the insertion of connecting element 36 with a specific curvature at a specific anatomical location.

Figure 21:
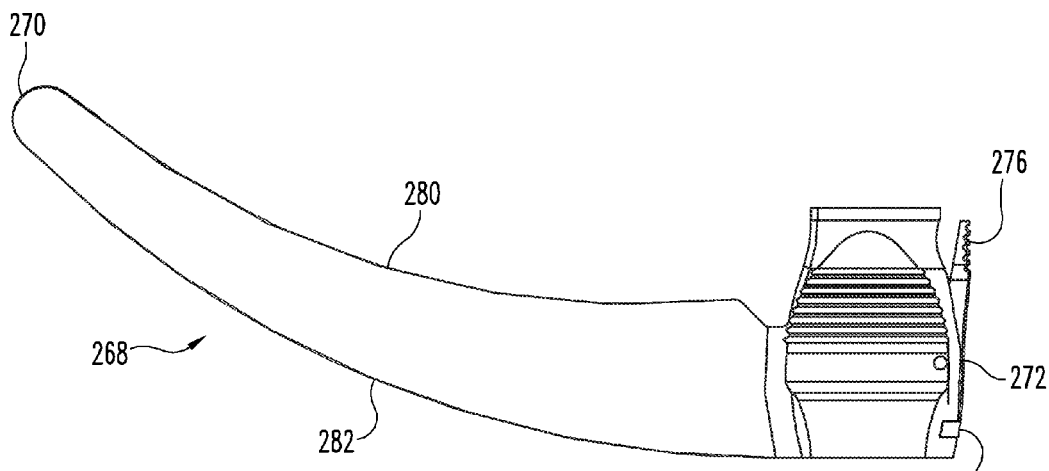
FIG. 21 is a side plan view of an alternative embodiment platform member suitable for use in the system of FIG. 1.
Figure 22:
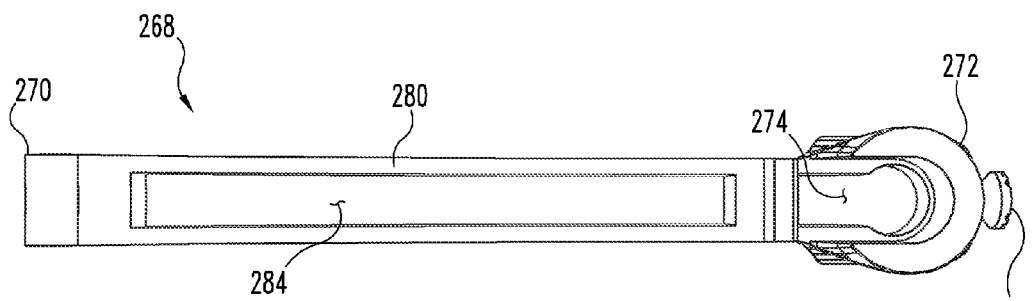
FIG. 22 is a top plan view of the alternative embodiment platform member of FIG. 21.
Figure 23:
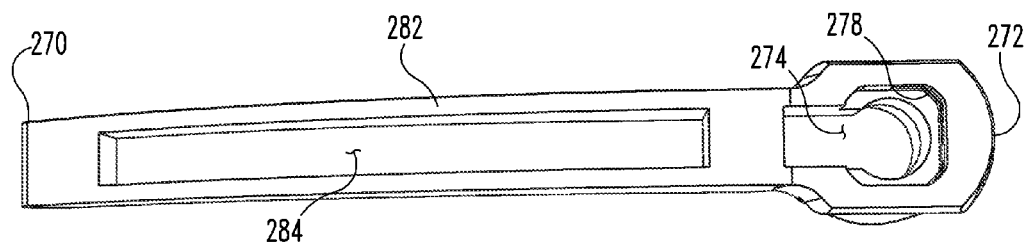
FIG. 23 is a bottom plan view of the alternative embodiment platform member of FIG. 21.

In addition to the foregoing, it should be appreciated that variations in the previously described arrangement of system 10 can be made. For example, an alternative embodiment platform member 268 is illustrated in FIGS. 21-23 and can be used in lieu of platform member 210. Platform member 268 extends between a first end 270 and a second end 272 that includes a passage 274 configured to be positioned over and receive post member 72 of elongated body 40. Second end 274 also includes a retaining element 276 that has a flange portion 278 that extends partially into passage 274. Retaining element 276 is normally biased by a biasing element (not shown) to the position illustrated in FIG. 21 such that flange portion 278 engages with one of grooves 74 or 76 on post member 72 of elongated body 40 in order to lock platform member 268 on anchor extender 20. However, retaining element 276 may be depressed in order to disengage flange portion 278 from groove 74 or 76 so platform member 268 may be released from anchor extender 20. In addition to the foregoing, it should be appreciated that passage 274 is configured to receive elongated housing 232 of inserter instrument 230 and guide it into engagement with anchor extender 20.

Similar to platform member 210, platform member 268 includes a proximal bearing surface 280 and an oppositely positioned distal surface 282. Platform member 268 also includes an elongated channel 284 positioned between first end 270 and second end 272 and extending between and opening at proximal bearing surface 280 and distal surface 282. Distal surface 282 generally includes a convex curvature and proximal bearing surface 280, which is configured to engage with a portion of inserter instrument 230, is concavely curved between first end 270 and second end 272. In the illustrated form, the curvature of proximal bearing surface 280 between first end 270 and second end 272 is varied. More particularly, the curvature of proximal bearing surface 280 adjacent first end 270 is greater than the curvature of bearing surface 280 adjacent second end 272, although embodiments where the curvature between first end 270 and second end 272 is constant are also contemplated. In other non-illustrated forms, it is contemplated that bearing surface 280 can be linear or provided with a non-continuous curvature; i.e., it can include one or more linear portions in combination with one or more curved portions. Still, in other forms, it is contemplated that system 10 can be provided with a plurality of platform members 268 that each includes an alternatively configured proximal bearing surface 280. In this arrangement, the orientation of engagement between inserter instrument 230 and proximal bearing surface 280 is adjustable, and a user can select an appropriately arranged platform member 268 to be used with a connecting element 36 having a specific curvature and/or to alter the insertion path of connecting element 36 as discussed in greater detail above.

Figure 24:
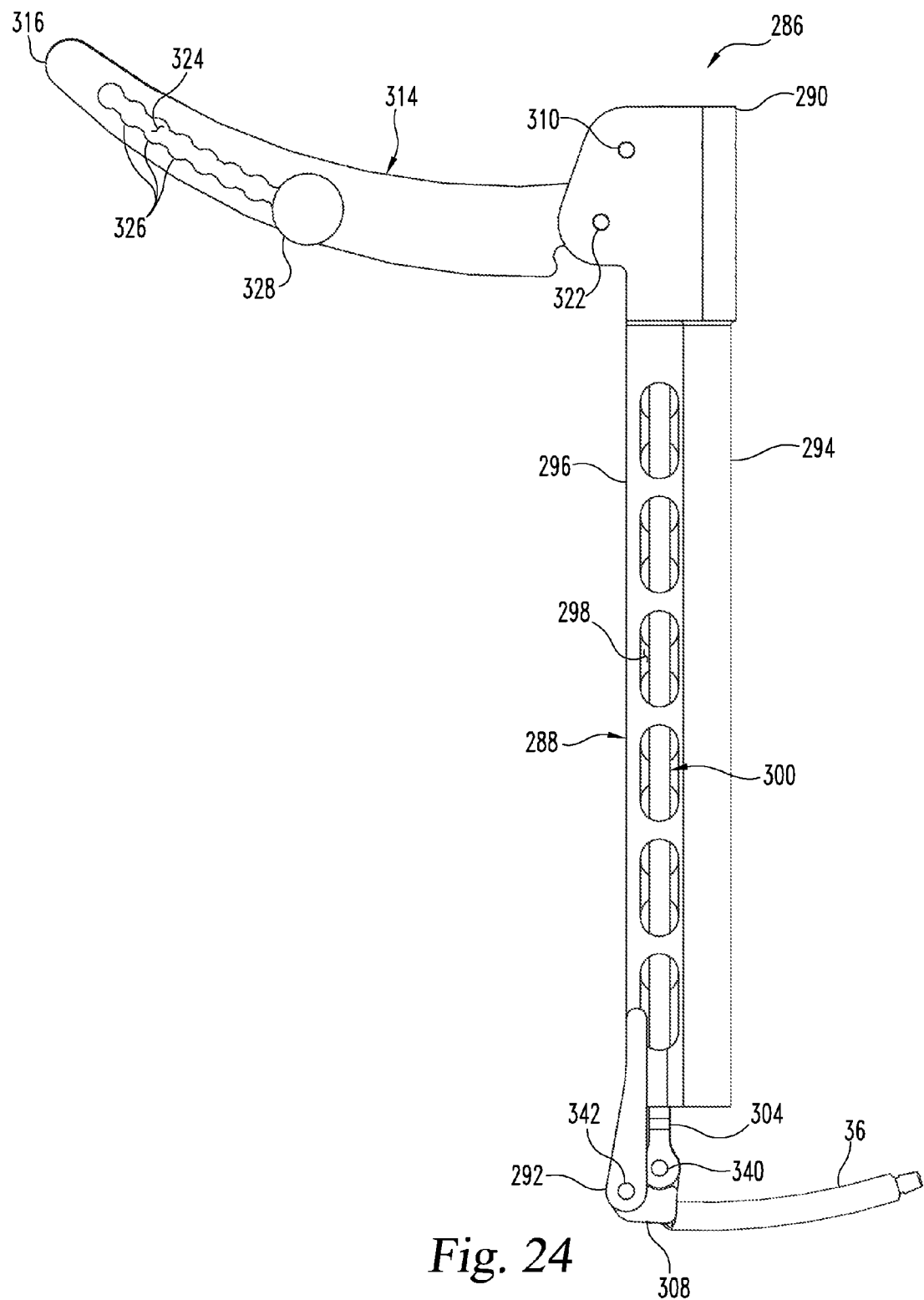
FIG. 24 is a side plan view of an alternative embodiment inserter instrument suitable for use in the system of FIG. 1.
Figures 25, 25A:
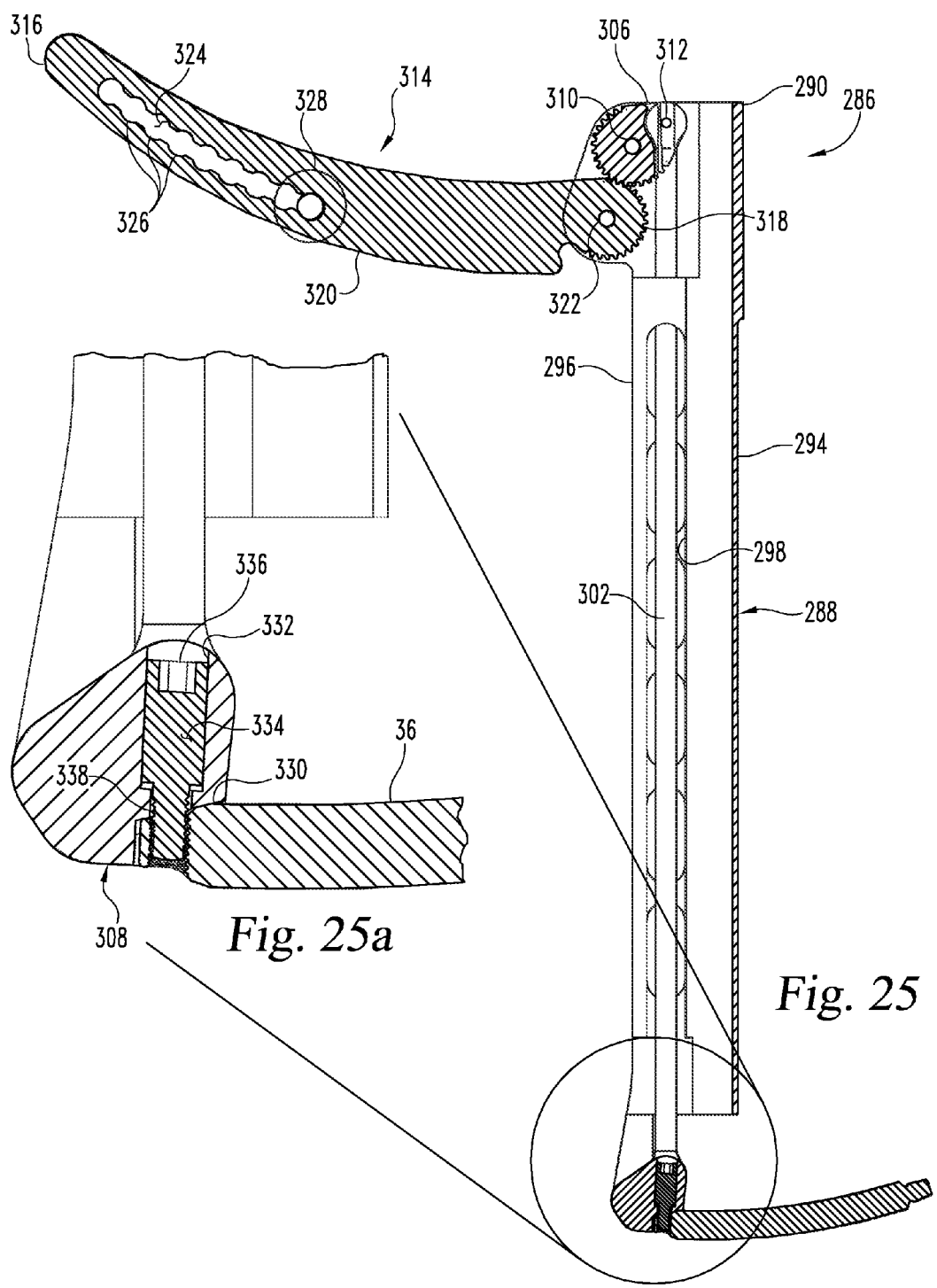
FIG. 25 is a section view of the alternative embodiment inserter instrument of FIG. 24.
FIG. 25a is an enlarged, section view of a distal portion of the alternative embodiment inserter instrument of FIG. 24.
Figure 26:
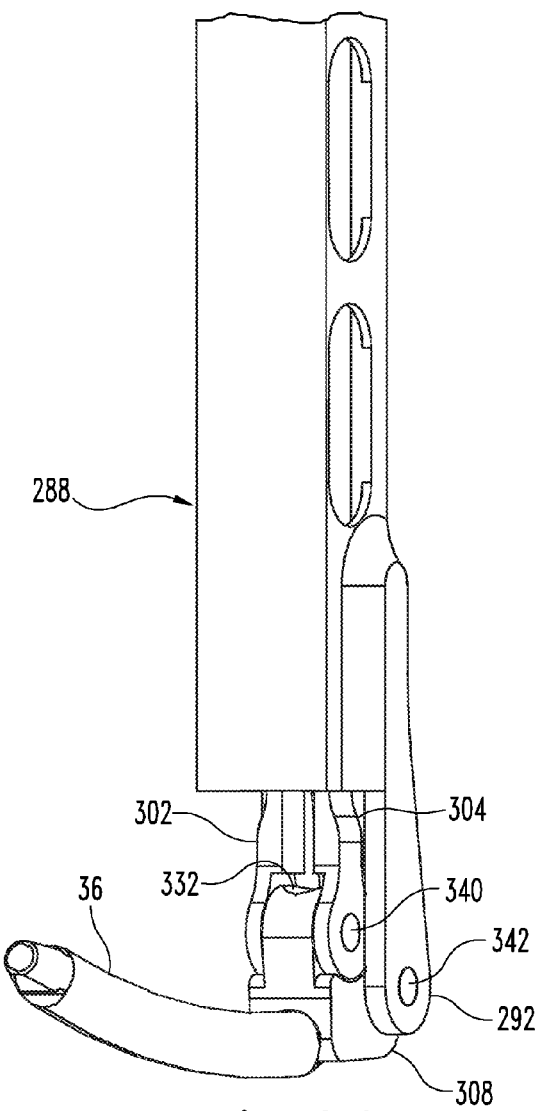
FIG. 26 is an enlarged, perspective view of a distal portion of the alternative embodiment inserter instrument of FIG. 24.

Referring now generally to FIGS. 24-26, further details regarding an alternative embodiment inserter instrument 286 that can be used in system 10 in lieu of inserter instrument 230 are provided. Inserter instrument 286 includes an elongated housing 288 that extends between a proximal end 290 and a distal end 292. Similar to elongated housing 232, elongated housing 288 also includes a first portion 294 that has a generally arcuate configuration and is positioned opposite of a second portion 296 that has a generally rectangular configuration. Similarly, when inserter instrument 286 is engaged with anchor extender 20, first portion 294 is received in hollow interior 66 of elongated body 40 while second portion 296 is positioned in and extends laterally through elongated slot 68 such that rotation of inserter instrument 286 relative to anchor extender 20 is prevented. Inserter instrument 286 also includes an elongated passage 298 within which a linking member 300 is positioned. Linking member 300 is defined by a pair of oppositely positioned arms 302, 304 that extend between a geared cam member 306 and a connecting element engaging member 308. Cam member 306 is pivotably coupled to elongated housing 288 by a pivot pin 310 and to arms 302, 304 by a pivot pin 312.

Inserter instrument 286 also includes a lever arm 314 that extends between a first end 316 and a geared second end 318, and includes a convexly curved surface 320. Second end 318 is pivotably coupled with elongated housing 288 by a pivot pin 322. In this configuration, geared second end 318 of lever arm 314 engages with geared cam member 306 such that geared cam member 306 is rotated relative to elongated housing 288 as lever arm 314 is moved relative to elongated body 288.

Figure 27:
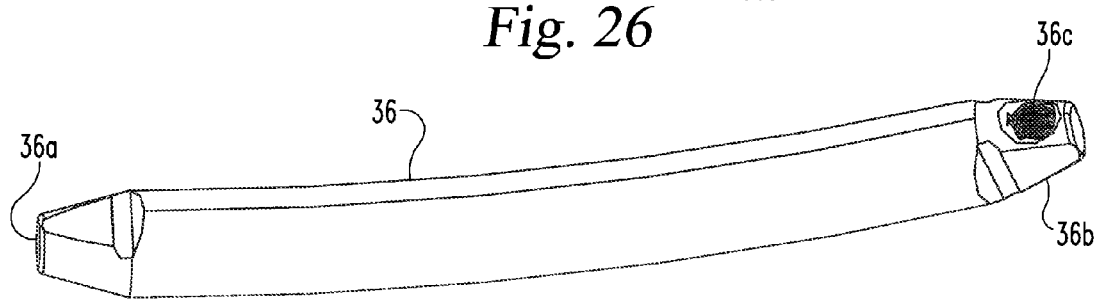
FIG. 27 is a plan view of a connecting element.

As best seen in the enlarged section view of FIG. 25a, connecting element engaging member 308 includes a receptacle 330 which releasably engages and receives end 36b of connecting element 36. More particularly, as illustrated in FIG. 27, ends 36a and 36b of connecting element 36 are generally conically shaped and receptacle 330 is provided with an internal shape that corresponds to the external conical shape of ends 36a, 36b. In addition, connecting element engaging member 308 also includes a passage 332 that generally extends transversely to receptacle 330 and includes a locking member 334 positioned therein. Locking member 334 includes a proximal tool engaging receptacle 336 which may be accessed with an appropriately configured driving tool, such as a screw driver (not shown), that is inserted through proximal end 290 of elongated housing 288 and advanced distally between arms 302, 304. Alternatively, it is also contemplated that connecting element engaging member 308 could be rotated away from elongated housing 288 such that locking member 334 in passage 332 could be laterally accessed by the driving tool instead of from between arms 302, 204. After connecting element 36 has been positioned in receptacle 360, locking member 334 can be rotated to advance a threaded portion 338 into engagement with an internally threaded passage 36c positioned on end 36b of connecting element 36 and extending generally transversely to the long axis of the same. Similarly, once connecting element 36 has been inserted to an appropriate location relative to anchors 30a, 30b with inserter instrument 286, the driving tool can been advanced distally between arms 302, 304 into engagement with receptacle 336 in order to disengage locking member 334 from connecting element 36 so inserter instrument 286 can be moved proximally away from connecting element 36.

Connecting element engaging member 308 is coupled with arms 302, 304 by a pivot pin 340 and to elongated housing 288 by a pivot pin 342. In this arrangement, connecting element engaging member 308 is rotated relative to elongated housing 288 in response to rotation of cam member 306 as lever arm 314 is moved relative to elongated housing 288. More particularly, as first end 316 of lever arm 314 is moved away from elongated housing 288, arms 302, 304 are moved proximally in passage 298 such that connecting element engaging member 308 is rotated away from elongated housing 288 and extends transversely to elongated housing 288 as illustrated in FIGS. 24-26. Similarly, when connecting element 36 is received in receptacle 330 and the orientation of connecting element engaging member 308 is changed relative to elongated housing 288, the orientation of connecting element 36 relative to elongated housing 288 also changes. Moreover, while not illustrated in FIGS. 24-26, it should be appreciated that when first end 316 of lever arm 314 is rotated toward elongated housing 288, arms 302, 304 will be moved distally in passage 298 such that connecting element engaging member 308 is also rotated toward elongated housing 288 and may be positioned in an orientation where it extends in general alignment with elongated housing 288. Accordingly, when connecting element 36 is received in receptacle 330 and connecting element engaging member 308 is positioned in this orientation, connecting element 36 will also extend in general alignment with elongated housing 288.

Lever arm 314 also includes an elongated slot 324 that includes a plurality of enlarged portions 326. A roller member or pin 328 is positionable along elongated slot 324 to any one of enlarged portions 326 in order to change the relationship between bearing surface 280 and lever arm 314 when inserter instrument 286 is used in combination with platform member 268. More particularly, as roller member 328 is positioned near the end of elongated slot 324 that is oriented toward geared second end 318, first end 316 of lever arm 314 will extend into elongated channel 284 of platform member 268 until roller member 328 comes into contact with bearing surface 280. Once roller member 328 contacts bearing surface 280, lever arm 314 will begin to pivot relative to platform member 268 such that first end 316 of lever arm 314 is moved away from elongated channel 284. Similarly, it should be appreciated that as roller member 328 is positioned closer to geared second end 318 of lever arm 314, it will require relatively increased distal movement of inserter instrument 286 relative to anchor extender 20 before lever arm 314 is rotated away from elongated housing 288. Thus, this configuration of lever arm 314 allows a user to adjust the relationship between lever arm 314 and platform member 268 in order to provide a configuration that is most suited for the insertion of connecting element 36 with a specific curvature at a specific anatomical location as discussed in greater detail above.

While not previously described, it should be appreciated that inserter instrument 286 can cooperate with anchor extender 20 to insert connecting element 36 adjacent to proximal receiving portions 32a, 32b of anchors 30a, 30b in a manner similar to that described above in connection with inserter instrument 230. Moreover, once connecting element 36 has been positioned at a desired location relative to anchors 30a, 30b, it can be disengaged from inserter instrument 286 and inserter instrument 286 can be removed from anchor extender 20.

As indicated above, a reduction instrument 344 may be engaged with anchor extender 22 and used to force connecting element 36 toward proximal receiving portions 32a, 32b of anchors 30a, 30b. However, it should also be appreciated that reduction instrument 344 may also be coupled with anchor extender 20 when platform member 210 or 268 and inserter instrument 230 or 286 are not engaged therewith. Accordingly, since various features of anchor extender 20 have already been explained in detail above, the use of reduction instrument 344 will be described in connection with anchor extender 20, although it should be appreciated that reduction instrument 344 can be engaged and used with anchor extender 22 in a similar manner. Reduction instrument 344 includes an elongated shaft portion 346 that extends distally from a housing member 356. Elongated shaft portion 346 extends between a threaded proximal portion 348 and a distal end portion 350 configured to engage with connecting element 36. Elongated shaft portion 346 also includes a raised portion 352 which is positioned in and extends along elongated slot 68 of elongated body 40 when reduction instrument 344 is engaged with anchor extender 20 such that elongated shaft portion 346 is prevented from rotating relative to anchor extender 20.

Figure 30:
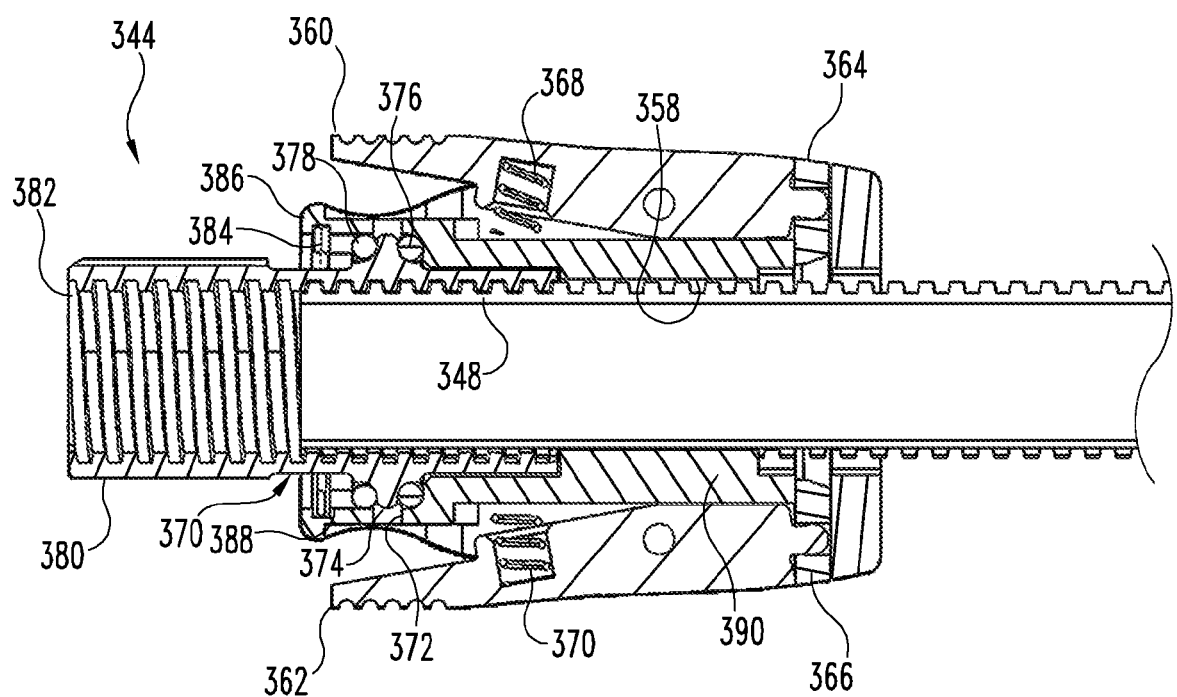
FIG. 30 is an enlarged, section view of a proximal portion of the reduction instrument of FIG. 28.

As illustrated in the section view of FIG. 30, housing member 356 includes a passage 358 in which threaded proximal portion 348 of elongated shaft portion 346 is positioned. Housing member 356 also includes a pair of oppositely positioned retaining elements 360, 362 that are coupled with flange portions 364, 366, respectively that extend partially into passage 358. Retaining elements 364, 366 are normally biased by biasing elements 368, 370, respectively, to the position illustrated in FIGS. 28-30 such that flange portions 364, 366 engage with grooves 74, 76 on post member 72 of elongated body 40 in order to lock reduction instrument 344 on anchor extender 20. However, retaining elements 368, 370 may be depressed in order to disengage flange portions 364, 366 from grooves 74, 76 so reduction instrument 344 may be removed from anchor extender 20.

Reduction instrument 344 also includes a driver member 370 positioned in passage 358 of housing member 356. Driver member 370 includes a proximal portion 380 that has a plurality of flat surfaces that may, amongst other functions, facilitate engagement of proximal portion 380 by an appropriately configured instrument used to rotate driver member 370. Driver member 370 also includes an internally threaded passage 382 which, as illustrated in FIG. 30, is engaged with a portion of threaded proximal portion 348. Driver member 370 is further provided with an annular ridge 374 which is positioned in an annular groove 372 of housing member 356. A plurality of ball bearings 376, 378 are positioned on opposite sides of annular ridge 374 and a spacer member 388 is positioned adjacent to ball bearings 378. A locking member 384 in the form of a snap ring for example, is positioned between spacer member 388 and an annular flange 386 on housing member 356 in order to retain driver member 370 in passage 358. In this configuration, driver member 370 is axially retained in passage 358 while also being rotatable relative to housing member 356.

Housing member 356 also includes a projection 390 that engages with an elongated groove 354 interrupting the threading on proximal portion 348 of elongated shaft portion 346 such that elongated shaft portion 346 is prevented from rotating relative to housing member 356. Similarly, it should be appreciated that elongated shaft portion 346 is axially displaced relative to housing member 356 as driver member 370 is rotated relative to housing member 356. Accordingly, driver member 370 can be rotated in a first direction in order to distally displace elongated shaft portion 346 relative to housing member 356 into engagement with connecting element 36 to position connecting element 36 in proximal receiving portions 32a, 32b of anchors 30a, 30b. Once connecting element 36 has been appropriately positioned, driver member 370 can be rotated in an opposite, second direction in order to proximally displace elongated shaft portion 346 relative to housing member 356 in order to disengage elongated shaft portion 346 from connecting element 36. Additionally or alternatively, it should be appreciated that housing member 356 can be disengaged from post member 72 and that reduction instrument 344 can be removed from anchor extender 20 or 22 once connecting element 36 has been positioned at a desired location without proximally displacing elongated shaft portion 346.

In one embodiment, systems for positioning a connecting element adjacent the spinal column in minimally invasive surgical procedures include one or more extenders removably engaged to one or more anchors engaged to a bony segment. The anchor extenders provide a reference to the respective anchor locations within the patient even when the anchor is obstructed by skin and/or tissue of the patient. Similarly, the anchor extenders are sized such that a portion thereof extends above the skin of a patient when they are engaged to the bone anchors. In one form, it is contemplated that separate incisions may be made for using and positioning each anchor and anchor extender. An inserter instrument is engageable with one of the anchor extenders and is movable along a longitudinal axis of the anchor extender. In response to movement of the inserter instrument along the longitudinal axis toward the bone anchors, a leading end of the connecting element is rotated away from the longitudinal axis until the connecting element is positioned at a location adjacent the number of bone anchors. In one aspect of this arrangement, the inserter instrument engages with the anchor extender such that the connecting element is introduced to the location adjacent the number of bone anchors through the same incision through tissue and muscle in which the respective anchor extender is positioned. Still, it should be appreciated that alternative forms, aspects, configurations, arrangements and methods are contemplated with respect to the subject matter disclosed and described herein.

Alternative configurations of the systems described herein are also contemplated. For example, in one or more forms the systems described herein can be configured to insert a connecting element that extends across and is engaged to anchors positioned at three or more vertebral levels or to three or more bony portions or segments. In addition, use of the systems described herein for stabilization of bones, bony structures or other anatomical features besides vertebral stabilization are contemplated. Furthermore, the systems and instrumentation described herein may also be used in surgical procedures involving animals, or in demonstrations for training, education, marketing, sales and/or advertising purposes. In addition, the systems and instrumentation described herein may be also used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. An anchor extender, comprising:
an elongated body extending between a proximal end portion and a distal end portion;
a first pair of engaging members coupled with said elongated body adjacent said distal end portion such that said first pair of engaging members are pivotable relative to one another, said first pair of engaging members being movable between a first configuration for receiving and releasing a first portion of a bone anchor and a second configuration for engaging said first portion of said bone anchor;
a second pair of engaging members coupled with said elongated body adjacent said distal end portion and opposite of said first pair of engaging members such that said second pair of engaging members are pivotable relative to one another, said second pair of engaging members being movable between a first configuration for receiving and releasing a second portion of said bone anchor and a second configuration for engaging said second portion of said bone anchor; and
a locking mechanism axially displaceable relative to said elongated body, wherein said locking mechanism is configured to lock said first and second pairs of engaging members in said second configuration.

2. The anchor extender of claim 1, wherein said elongated body includes a first leg member positioned opposite of a second leg member, and said first pair of engaging members are pivotably coupled to said first leg member and said second pair of engaging members are pivotably coupled to said second leg member.

3. The anchor extender of claim 1, wherein said elongated body includes a hollow interior and a first elongated slot communicating with said hollow interior, said first elongated slot extending through a first side of said elongated body from said proximal end portion to said distal end portion.

4. The anchor extender of claim 3, wherein said elongated body further includes a second elongated slot extending through a second side of said elongated body opposite of said first elongated slot, said second elongated slot communicating with said hollow interior and extending proximally from said distal end portion and terminating distally of said proximal end portion.

5. The anchor extender of claim 1, further comprising a first biasing element positioned between said first pair of engaging members and a second biasing element positioned between said second pair of engaging members, said first and second biasing elements biasing said first and second pairs of engaging members toward said second configuration.

6. The anchor extender of claim 1, wherein said locking mechanism includes a pair of elongated locking members each extending between a proximal end and a distal end, and a cap member engaged with said proximal ends of said elongated locking members and positioned about said proximal end portion of said elongated body.

7. The anchor extender of claim 6, wherein each of said distal ends of said pair of elongated locking members includes a first tab spaced apart from a second tab, said first and second tabs being receivable in receptacles formed in respective ones of said first and second pairs of engaging members as said locking mechanism is distally displaced relative to said elongated body in order to lock said first and second pairs of engaging members in said second configuration.

8. The anchor extender of claim 6, wherein each one of said elongated locking members includes a raised surface configured to engage with a recess positioned between respective ones of said first and second pairs of engaging members as said locking mechanism is distally displaced relative to said elongated body in order to force said first and second pairs of engaging members toward said second configuration.

9. The anchor extender of claim 6, further comprising a retaining member releasably engageable with said cap member of said locking mechanism in order to retain said locking mechanism in a position relative to said elongated body where said first and second pairs of engaging members are locked in said second configuration by said elongated locking members.

10. The anchor extender of claim 1, wherein said first pair of engaging members are spaced apart from one another when said first pair of engaging members are in said first configuration and engage one another when in said second configuration.

11. The anchor extender of claim 1, wherein said second pair of engaging members are spaced apart from one another when said second pair of engaging members are in said first configuration and engage one another when in said second configuration.

12. The anchor extender of claim 1, wherein said elongated body includes opposite first and second elongated slots extending into an outer surface of said elongated body, said anchor extender further comprising a cap member and first and second elongated locking members coupled to said cap member, said first and second elongated locking members being slidably positioned in said first and second elongated slots.

13. The anchor extender of claim 12, wherein tips of said first and second elongated locking members engage said first and second pairs of engaging members when said first and second pairs of engaging members are in said first configuration and are spaced apart from one another when said first and second pairs of engaging members are in said second configuration.

14. The anchor extender of claim 12, wherein said cap member comprises a distally extending stem and said anchor extender further comprises a retaining element that pivotably engages said elongated body, wherein said retaining element engages a notch on said stem when said first and second pairs of engaging members are in said second configuration and retaining element is spaced apart from said notch when said first and second pairs of engaging members are in said first configuration.

15. The anchor extender of claim 14, wherein said retaining element is biased to a position in which said retaining element engages said notch.

16. The anchor extender of claim 14, wherein said retaining element is biased by a spring to a position in which said retaining element engages said notch.

17. The anchor extender of claim 12, wherein said cap member includes a passageway with the elongated body disposed therein such that the cap member is axially translatable relative to the elongated body.

18. The anchor extender of claim 2, wherein said first and second legs define opposite elongated slots that are in communication with a hollow interior of said elongated body such that a spinal rod may be positioned through said elongated slots and said hollow interior.

19. The anchor extender of claim 2, wherein said elongated body includes opposite first and second elongated slots extending into an outer surface of said elongated body, said anchor extender further comprising a cap member and first and second elongated locking members coupled to said cap member, said first and second elongated locking members being slidably positioned in said first and second elongated slots.

20. The anchor extender of claim 19, wherein tips of said first and second elongated locking members engage said first and second pairs of engaging members when said first and second pairs of engaging members are in said first configuration and are spaced apart from one another when said first and second pairs of engaging members are in said second configuration.

* * * * *